(12) United States Patent
Jog et al.

(10) Patent No.: US 7,756,588 B2
(45) Date of Patent: Jul. 13, 2010

(54) METHOD OF FABRICATING A MULTICHANNEL ELECTRODE

(75) Inventors: Mandar Jog, London (CA); Suwas Nikumb, London (CA)

(73) Assignees: London Health Sciences Center, London (CA); National Research Council of Canada, Ottawa (CA)

( * ) Notice: Subject to any disclaimer, the term of this patent is extended or adjusted under 35 U.S.C. 154(b) by 1038 days.

(21) Appl. No.: 11/245,228

(22) Filed: Oct. 6, 2005

(65) Prior Publication Data

US 2006/0095105 A1 May 4, 2006

Related U.S. Application Data

(62) Division of application No. 10/001,050, filed on Oct. 31, 2001, now Pat. No. 7,010,356.

(51) Int. Cl.
*A61N 1/05* (2006.01)
(52) U.S. Cl. .................... 607/117; 607/116; 600/377; 600/378; 600/393
(58) Field of Classification Search .................... None
See application file for complete search history.

(56) References Cited

U.S. PATENT DOCUMENTS

| | | | |
|---|---|---|---|
| 1,622,446 A | 3/1927 | Wappler | |
| 4,332,259 A | 6/1982 | McCorkle, Jr. ............. | 128/786 |
| 4,355,646 A | 10/1982 | Kallok et al. ............... | 128/786 |
| 4,444,195 A | 4/1984 | Gold ........................ | 128/642 |
| 4,649,937 A | 3/1987 | DeHaan et al. ............. | 128/784 |
| 5,282,468 A | 2/1994 | Klepinski ................... | 128/642 |
| 5,405,375 A | 4/1995 | Ayers et al. ................. | 607/122 |
| 5,462,545 A | 10/1995 | Wang et al. .................. | 606/41 |
| 5,836,875 A | 11/1998 | Webster, Jr. ................ | 600/374 |
| 6,240,320 B1 | 5/2001 | Spehr et al. ................. | 607/122 |
| 6,249,708 B1 | 6/2001 | Nelson et al. ............... | 607/122 |
| 6,473,653 B1 | 10/2002 | Schallhorn et al. .......... | 607/116 |
| 6,516,232 B2 * | 2/2003 | Skinner ...................... | 607/122 |
| 6,711,443 B2 | 3/2004 | Osypka ...................... | 607/122 |

OTHER PUBLICATIONS

Albe-Fessard et al., *Electrophysiological Localization and Identification of Subcortical Structures in Man by Recording Spontaneous and Evoked Activities*, 1963, Electroenceph. Clin. Neurophysiol, vol. 15, pp. 1052-1053.

(Continued)

*Primary Examiner*—Kennedy J Schaetzle
(74) *Attorney, Agent, or Firm*—Edwards Angell Palmer & Dodge LLP; Elizabeth Spar; Kathleen Williams

(57) ABSTRACT

The invention provides a multichannel electrode ("MC electrode") which can perform multiple functions such as recording, stimulating and lesioning simultaneously or sequentially upon a single insertion into a target site. In one aspect, the MC electrode further provides imaging and drug delivery capabilities. The invention also provides interface connectors for connecting the MC electrode to external units such as data acquisition and/or stimulation systems. Although the MC electrode and associated connectors and system(s) provide an optimal way to perform deep brain surgical procedures, the MC electrode and associated connectors and system(s) are useful generally in any technique which relies on recording, activating, and/or inhibiting electrical signals produced by cells.

5 Claims, 15 Drawing Sheets

Concentric fiber based design

Both fibers are hollow with conducting channels machined on the surface.

OTHER PUBLICATIONS

Ablin et al., *The Functional Anatomy of Disorders of the Basal Ganglia*, 1995, Trends Neurosic, vol. 18, pp. 63-64.

Alexander et al., *Basal Ganglia-Thalamocortical Circuits: Parallel Substrates for Motor, Oculomotor, "Prefrontal" and "Limbic" Functions*, 1990, Prog. in Brain Res., vol. 85, pp. 119-146.

Gross et al., *Relationship of Lesion Location to Clinical Outcome Following Microelectrode-Guided Pallidotomy for Parkinson's Disease*, 1999, Brain, vol. 122, pp. 405-416.

Gross et al., *Variability in Lesion Location After Microelectrode-Guided Pallidotomy for Parkinson's Disease: Anatomical, Physiological, and Technical Factors that Determine Lesion Distribution*, J. Neurosurg, vol. 90, pp. 468-477, 1999.

Lang et al, *Parkinson's Disease*, 1998, The New England Journal of Medicine, vol. 339, No. 16, pp. 1130-1143.

Jasper et al., *Exploration of the Human Thalamus with Microelectrodes*, 1963, Physiologist, vol. 7, p. 167.

James B. Ranck, *Which Elements are Excited in Electrical Stimulation of Mammalian Central Nervous System: A Review*, 1975, Brain Research, vol. 98, pp. 417-440.

\* cited by examiner

The drawing shows close up of quadraelectrodes on a hollow fiber. Note the four channels in every quadraelectrode.

A single fiber is shown with multiple alternating RTQs and STQs

Machined gold-plated copper flex circuit board mounted on cylindrical conductor

Electrode tip geometry on the flex circuit board. Note Ch 4 on the metal rod backbone.

Animal connected to data acquisition system

Electrode penetrating brain

Single neuron spike (time 200 µs/div vs voltage 50µV/div)

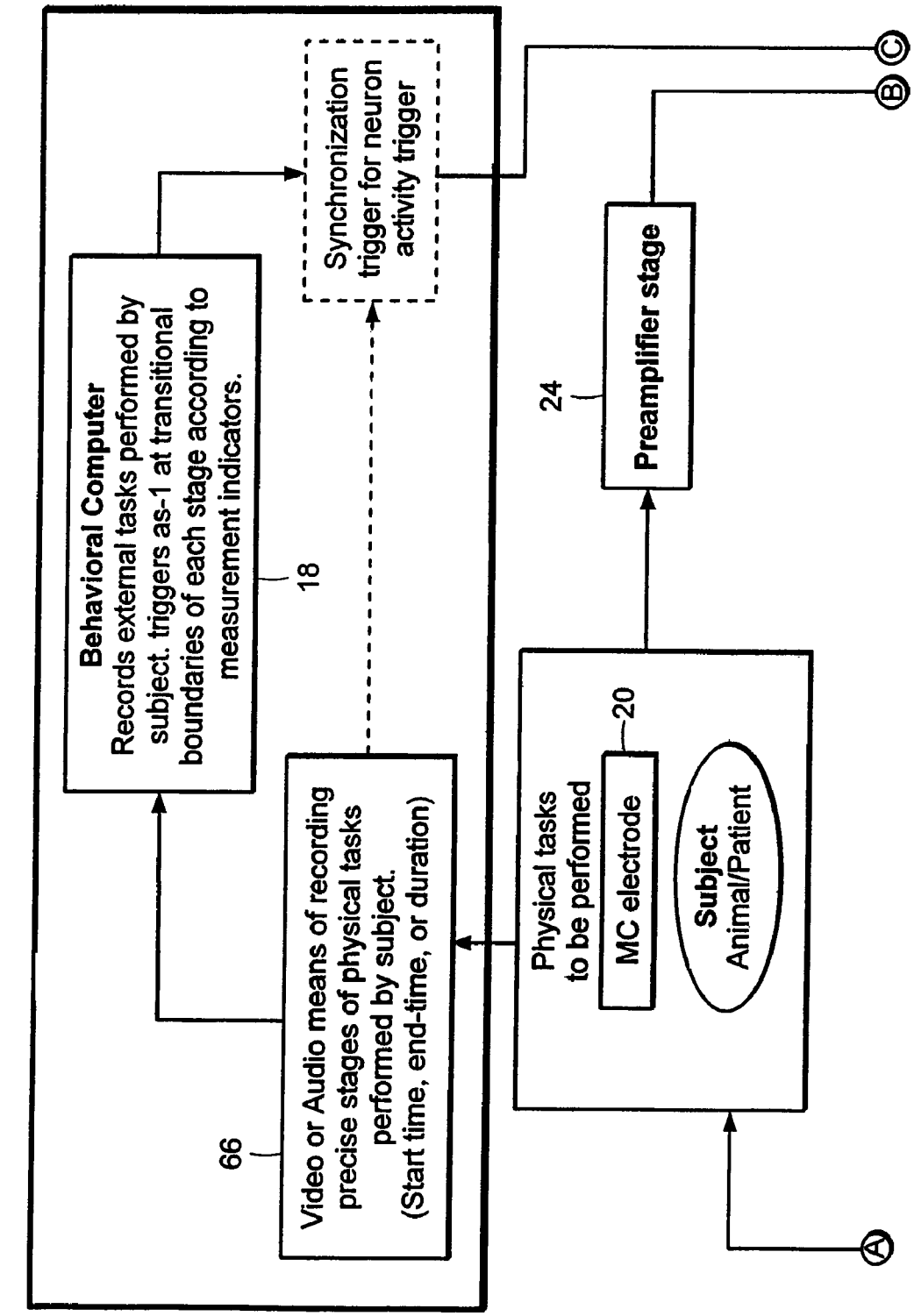

000
METHOD OF FABRICATING A MULTICHANNEL ELECTRODE

RELATED APPLICATIONS

This application is a Divisional of U.S. patent application Ser. No. 10/001,050, filed Oct. 31, 2001, now U.S. Pat. No. 7,010,356, the entirety of which is incorporated herein by reference.

FIELD OF THE INVENTION

The invention relates to a multichannel electrode comprising a non-planar backbone for use in medical procedures, particularly neurosurgical procedures.

BACKGROUND OF THE INVENTION

During neurosurgical procedures, electrodes are commonly used to monitor electrical activity and stimulate and/or lesion neural tissue. Typically, electrodes are brought into the vicinity of cell membranes so that an electrical transition resistance (impedance) is created between the cells and the electrodes. Electrical stimulation of a malfunctioning neuron can be used to activate or reversibly block neural activity, while lesioning can be used to permanently disable neuronal activity. U.S. Pat. No. 1,662,446, issued to Wappler, teaches an early electrode system.

The recent resurgence of procedures to stimulate and produce lesions in deep brain structures for the treatment of Parkinson's disease, tremor, and dystonia, has been due not only to a better understanding of functional neuroanatomy of the cells involved in these diseases (Albin et al., 1995, *Trends in NeuroScience* 18(2): 63-4; Alexander et al., 1990, *Prog. in Brain Res.* 85: 119-46) but also to the development of techniques for accurately localizing these cells (Lang et al., *N. Engl. J. Med.* 339(16): 1130-43). Microelectrode recording allows direct recording and characterization of the activity of neural cells and can be used to record individual cells at a spatial interval from a micron to 100 microns and in a frequency range from 1 Hz to 200 Hz (see, e.g., Albe-Fessard et al., 1963, *Ann. Chir.* 17: 1185-1214; Albe-Fessard et al., 1963, *Electroencephalogr. Clin. Neurophysiol.* 15: 1052; Jasper et al., 1963, *Physiologist* 7: 167).

While microelectrodes provide the best means of localizing diseased cells, generally, microelectrodes must be inserted into the brain multiple times (e.g., at target sites separated by about 2 mm) to sufficiently characterize the physiology of a region which is to be stimulated or lesioned. Probes comprising groups of microelectrodes bundled together at high density ("multichannel microelectrodes") increase the resolution of individual recording passes, and can stimulate and record a 20-200 µm radius around an insertion site (see, e.g., Gross et al., 1999, *Brain* 122(Pt3): 405-16; Gross et al., 1999, *J. Neurosurg.* 90(3): 468-77; Ranck, 1975, *Brain Res.* 98: 417-440). Typically, a multichannel microelectrode is inserted at a location, and when a site of pathology is identified, it is removed and replaced by a larger diameter macroelectrode (e.g., about 1.1 mm) which is used to validate target location and for subsequent stimulating and/or lesioning as appropriate. However, even multichannel microelectrodes must be inserted and removed at least three to five times to obtain good target localization and macroelectrodes generally must be inserted separately.

Multichannel electrodes which combine the recording functions of microelectrodes and the stimulating functions of macroelectrodes have been reported. Generally, these systems consist of recording and stimulating wires which radiate from a planar backbone (see, e.g., U.S. Pat. No. 5,282,468). Because of the large surface area these electrodes occupy, they generally are suited only for recording and stimulating neurons at the surface of the brain and are not for use in deep brain procedures.

SUMMARY OF THE INVENTION

The invention provides a multichannel electrode ("MC electrode") which can perform multiple functions such as recording, stimulating and lesioning upon a single insertion into a target site. In one aspect, the MC electrode further provides imaging, drug delivery and therapeutic capabilities. For example, the MC electrode can be used to provide growth factors, chemotherapeutics, epilepsy drugs, and/or radiation or radiofrequency therapy to a target site.

The invention also provides interface connectors for connecting a first end of an MC electrode to external units such as data acquisition and/or stimulation systems. Although the MC electrode and associated connectors and system(s) provide an optimal way to perform deep brain surgical procedures, the MC electrode and associated connectors and system(s) are useful generally in any technique which relies on recording, activating, and/or inhibiting electrical signals produced by cells.

In one aspect, the MC electrode according to the invention comprises a non-planar, substantially cylindrical backbone which comprises a plurality of electrode channels. Preferably, the backbone is flexible, or semi-flexible, and comprises a substantially conical or frustoconical tip for ease of insertion at a site comprising one or more target cells. More preferably, however, the MC electrode has sufficient stiffness to avoid deviation from a stereotactic perspective.

In one aspect, the backbone comprises a non-conductive material. In another aspect, the backbone comprises a lumen. In a further aspect, the backbone alternatively, or additionally, is capable of transmitting light. For example, the backbone can be a light guide or an optical fiber. In still a further aspect, the backbone is capable of delivering an agent (e.g., such as a drug) to a site comprising one or more target cells.

Preferably, the non-planar backbone comprises an electrically conductive layer. In one aspect, the non-planar backbone is bonded to an electrically conductive material and electrode channels are micromachined or microlithographically etched into the electrically conductive material. Preferably, the channels are micromachined by laser micromachining or other methods. In another aspect, the non-planar backbone comprising electrode channels is contained partially within a probe housing with at least its tip exposed. The probe housing can be designed to facilitate handling by a user and for connection to a drive system used to activate and control the movement of the MC electrode. Preferably, the MC electrode can be advanced and retracted and/or rotated to enhance its ability to localize a target. This can be achieved by providing an interfacing connector in communication with a microdrive device.

Preferably, the MC electrode comprises sets of channels, each set comprising at least two, and preferably, at least four electrode channels. In a preferred aspect, at least two of the channels in each set are at least partially non-coplanar relative to each other.

In one aspect, the backbone of the MC electrode comprises a second end comprising a conical or frustoconical tip. The tip comprises a base portion adjacent to a substantially cylindrical portion of the backbone and a tip portion comprising a diameter which is smaller than the base portion. The electrode comprises at least one set of four channels disposed on the backbone. At least one channel extends past the base portion of the tip while at least one channel does not extend past the base portion of the tip.

Each set of channels preferably performs a specific function, such as recording or stimulating/lesioning. Preferably, the MC electrode comprises at least one set of channels for recording ("recording channel sets") and at least one set of channels for stimulating and/or lesioning ("stimulating/lesioning channel sets"). Still more preferably, a plurality (i.e., at least two) of recording channel sets and stimulating/lesioning channel sets are provided.

In a preferred aspect of the invention, sets of four electrode channels or "quadraelectrodes" are disposed on the non-planar backbone and at least two of the channels are at least partially non-coplanar with each other. Preferably, at least three of the channels are on a single plane while the fourth channel is at least partially on a different plane. In one aspect of the invention, the quadraelectrodes are either recording type quadraelectrodes (RTQs) or stimulating type quadraelectrodes (STQs). Generally, RTQs do not perform stimulating or lesioning functions while STQs do not perform recording functions. However, preferably STQs have both stimulating and lesioning capabilities.

Preferably, RTQs record from all four channels simultaneously, providing an electronic signature or image of one or more neurons in proximity to the RTQ to allow the precise localization of the one or more neurons. The directionality of a plurality of signal sources also can be determined. By precise resolution of the multiple signals recorded, a functional map or image of a population of neurons being studied can be obtained. This functional map can be correlated with a patient's symptoms and can be used to determine appropriate STQs to use to stimulate the appropriate populations of neurons.

Generally, STQs comprise at least one channel with a positive polarity and at least one channel with a negative polarity. Combinations of three positive channels and one negative channel, three negative channels and one positive channel, or two negative channels and two positive channels can be provided.

In one aspect, the sets of electrode channels are electrically insulated from each other. Individual electrode channels also may partially covered by an insulating material. For example, the channels can be covered over the cylindrical portion of the backbone and exposed at least partially at the conical or frustoconical tip portion of the backbone.

The invention also provides methods for fabricating a multichannel electrode. In one aspect, the method comprises the steps of: providing a non-planar backbone, coating the non-planar backbone with an electrically conductive material, and laser micromachining a plurality of channels into the electrically conductive material. Preferably, the electrically conductive material is bonded to the non-planar backbone by direct deposition techniques or by coating an adhesive layer onto the backbone. Preferably, at least one channel comprises an impedance suitable for recording electrical activity of a cell, and at least one channel comprises an impedance suitable for stimulating the electrical activity of a cell.

In one aspect, the invention provides a multichannel electrode comprising:

a first non-planar backbone comprising a lumen, and a second non-planar backbone disposed within the lumen of the first non-planar backbone. The first and second backbone each comprise at least one electrode channel, wherein at least one of the channels has an impedance suitable for recording an electrical signal from a cell, while at least one other of the channels has an impedance suitable for electrical stimulation of a cell.

In another aspect, the multichannel electrode comprising the first and second backbone comprises one or more sets of channels, wherein at least one of the sets of channels has an impedance suitable for recording and at least one of the sets has an impedance suitable for stimulating. In a further aspect, a set can comprise at least two channels, at least one channel being on the first backbone and at least a second channel being on the second backbone.

The first and second backbone can be machined separately. However, the first and second backbone also can be formed by rolling a flat planar sheet which channels have been machined around a central fiber. The central fiber itself can comprise one or more channels.

The invention also provides an interfacing connector for interfacing the MC electrode with one or more external systems, such as an interfacing cable, drives, processors, multichannel stimulation units, light sources, detectors, oscilloscopes, fluid delivery pumps, suction devices, filters, a power supply, radiation treatment sources, amplifiers, displays, implantable source devices (e.g., providing stimulating and recording functions for use in chronic therapies) and the like. In one aspect, the interfacing connector is coupled to the one or more external devices by means of the interfacing cable.

In one aspect, the interfacing connector comprises a plurality of wires, each wire connected to a channel of the multichannel electrode at one end and connectable to at least one external system at another end.

In another aspect, the connector comprises a substantially cylindrical housing with a first and second end and an outer wall. A plurality of central terminals radiate from the other wall to form an inner wall defining a lumen. The central terminals form electrical contacts with the plurality of channels of the MC electrode. The first end of the interfacing connector housing receives the MC electrode in the central opening, while the second end of the interfacing housing is coupleable to at least one external system.

Preferably, a processor which is in communication with the interfacing connector (either directly or via the cable) is used to send and receive signals to other external components of the system and can direct the activity of the MC electrode in response to these signals. For example, the processor can be used to regulate the recording and stimulating/lesioning functions of the sets of electrode channels of the MC electrode. The processor also can be used to control the motion of the MC electrode in response to optical data and/or electrical data received from one or more neural cells. In a preferred aspect, the interfacing connector comprises components for enhancing or regulating electrical signals sent or received by the channels of the electrode. For example, the interfacing connector can comprise resistors in communication with the channels for modulating the impedance of the channels so that a particular set of channels functions optimally as a recording channel set or as a stimulating channel set, respectively. The interfacing connector also can comprise one or more preamplifiers for amplifying signal received from a recording channel set.

In one aspect, the non-planar backbone of the MC electrode comprises a first end and a second end and is at least partially transparent. The first end is in optical communication with a light source (e.g., such as a laser, a non-coherent light source, and the like) while the second end comprises the conical or frustoconical tip portion of the electrode. The backbone provides a light path for transmitting light from the light source to a target and for receiving light from the target. A received light path can be coincident with, or separate from, a transmitted light path. For example, the backbone can be a light guide or an optical fiber or can comprise a bundle of light guides or optical fibers.

Preferably, a detector also is in optical communication with at least the received light path, and converts optical signals received into signals (e.g., electrical signals) which can be translated into an image of the target site. Preferably, the processor is used to display this image on the display of a user device (e.g., such as a computer) coupled to the processor, enabling a user of the electrode to visualize the target site and adjust the movement and/or activity of the electrode as necessary.

In one aspect, the backbone is hollow to facilitate the transmission of light (e.g., the backbone itself can be a hollow optical fiber to provide annular ring light). In another aspect, a light path is provided in the form of a fiber which is itself placed within the hollow backbone. In still another aspect, bundles of optical fibers are provided within the lumen of the hollow backbone. In a further aspect, a backbone is provided which comprises a groove or channel along its side into which a light guide or optical fiber can be fitted. The light guide or fiber can be coupled to a camera to facilitate the imaging process.

When the backbone is hollow, a pump can be coupled to a first end of the backbone or to a portion of the interface connector, to facilitate the transport of fluids through the lumen of the backbone. In this way, the MC electrode also can be used as a drug delivery device or to provide irrigation fluids to wash a target site. However, a delivery device in the form of a hollow flexible capillary or hollow needle also can be inserted into the lumen of the backbone and connected to the pump. The delivery device also can be fitted into a groove or channel along the side of the backbone.

Preferably the interfacing connector is connected or connectable to a drive mechanism which controls guided precise movement of the electrode during surgical procedures and chronically once the MC electrode is left in situ.

In one aspect, the processor is part of a data acquisition system which implements one or more programs for analyzing electrical signals obtained from one or more neurons at a target site and for characterizing the one or more neurons as diseased or healthy. In a preferred aspect, the processor is capable of characterizing a plurality of signals obtained simultaneously from different sets of channels in the multi-channel electrode and even from groups of multichannel electrodes. In one aspect, the processor displays the output of this analysis on the display of a user device (e.g., a computer) connectable to the network.

In one aspect, the data acquisition system is in communication with the MC electrode and, in conjunction with the processor, captures and processes neuronal signals acquired by the MC electrode. Preferably, the processor conditions or instructs the data acquisition system to capture neuronal signals at selected times.

The invention also provides a method for acquiring neuronal activity data from a subject comprising the steps of: sensing neuronal signals generated by a subject as the subject performs a task, recording at least one physical condition of the subject while the task is being performed, and correlating the neuronal signals with at least one recorded physical condition to yield anatomical information concerning structures from which the neuronal signals originate.

The MC electrodes according to the invention can be used for acute or chronic treatment regimens. For example, where chronic stimulation of one or more cells is desired (e.g., in the treatment of chronic pain) or where long-term monitoring is required (e.g., for an individual with seizures), the MC electrode can be coupled to a source device (e.g., a stimulator/recording device) via percutaneous leads which are connected to the interfacing connector. Preferably, leads are placed within a biocompatible, sterilizable, flexible or semi-flexible sheath. The source device preferably comprises a battery for providing a source of power to the MC electrode and/or a microprocessor for providing instructions to the MC electrode to perform selected recording and/or stimulating functions. However, in another aspect, the microprocessor is part of an extracorporeal device which is controlled by the patient or a health care worker.

The invention further provides a method of monitoring the activity of one or more cells at a target site by recording electrical potentials of the one or more cells and/or modulating the activity of one or more cells. In one aspect, the method comprises bringing an MC electrode as described above in electrical proximity to the one or more cells and recording the activity of the one or more cells using at least one recording channel set (e.g., such as an RTQ) of the MC electrode. Preferably, this recorded activity is compared to the activity of a cell with one or more known physiological properties (e.g., a non-diseased neural cell). In one aspect, the recorded activity is used to determine the anatomical location of one or more malfunctioning cells. In a preferred aspect, after determining the anatomical location of the one or more malfunctioning cell, at least one other set of channels (e.g., a stimulating/lesioning channel set, such as an STQ) is activated to deliver an electrical stimulus to the one or more cells. In one aspect, the stimulus is used to activate the one or more cells. In another aspect, the stimulus is used to inhibit the one or more cells. In a further aspect, the stimulus is used to disable or lesion the one or more cells.

Preferably, a processor in communication with the MC electrode is used to control the movement and activity of the electrode. In a particularly preferred aspect, the MC electrode is used to image a target site and the processor moves and/or alters the activity of the electrode in response to an image obtained (i.e., automatically, or in response to instructions from a user).

The method of the invention can be used to treat of a number of neurological disorders including, but not limited to, motor dysfunction, spasticity, Parkinsonism, tremors, dystonia, mood disorders, hypothalmic obesity, incontinence, chronic pain, spinal cord injuries, epilepsy, and the like.

In one aspect, the MC electrode is used in an acute treatment by bringing the MC in proximity to one or more cells, localizing target cells in need of such treatment (e.g., using at least one RTQ), bringing the MC in closer proximity to the cells if necessary, activating or inhibiting the activity of the target cells or disabling the target cells (e.g., using at least one STQ), and removing the MC electrode from the proximity of the target cells.

In another aspect, the MC electrode is used in a chronic treatment by bringing the MC in proximity to one or more cells, localizing target cells in need of such treatment (e.g., using at least one RTQ), bringing the MC electrode in closer proximity to the cells if necessary, and activating or inhibiting the activity of the target cells (e.g., using at least one STQ). Preferably, the MC electrode remains in proximity to the target cells to monitor the activity of the target cells and to stimulate the cells as necessary to maintain a desired state of the cells.

In addition to using the MC electrode in methods of treatment, the MC electrode can be used to detect the presence of, or monitor the progression of, abnormal physiological activity in a cell. In a further aspect, the MC electrode is used to monitor the electrical activity of cells at a target site in order to control drug delivery to the target site.

BRIEF DESCRIPTION OF FIGURES

The objects and features of the invention can be better understood with reference to the following detailed description and accompanying drawings. The drawings are not to scale.

DETAILED DESCRIPTION OF THE INVENTION

Figure 1:
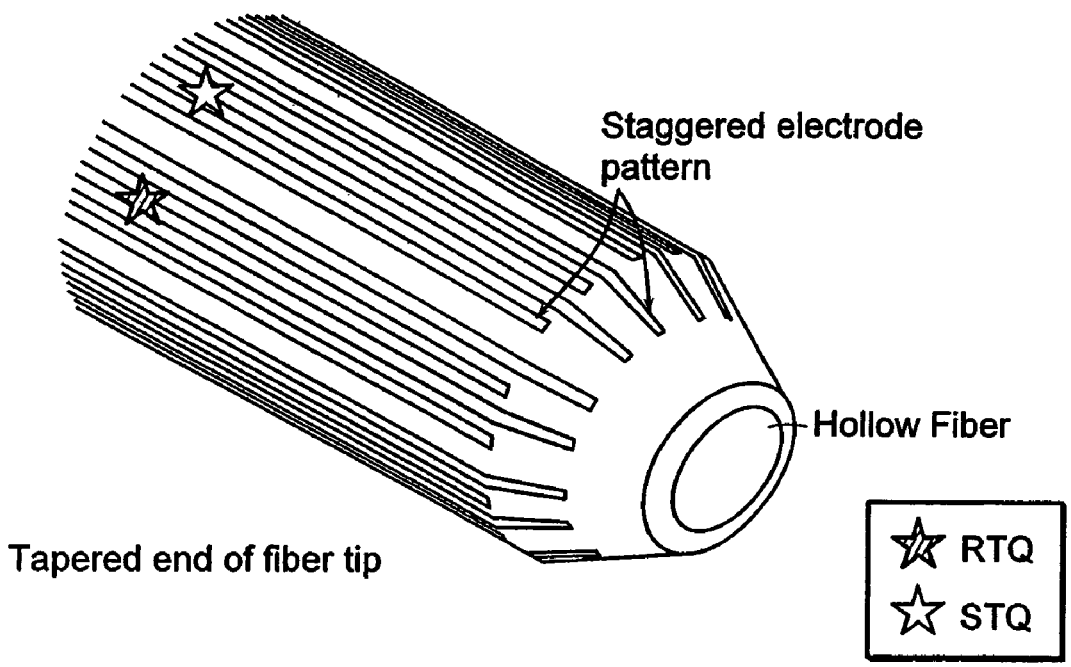
FIG. 1 depicts a close up of sets of electrode channels on an optical fiber backbone according to one aspect of the invention. In this Figure, each set or "quadraelectrode" comprises four channels. The larger stars represent quadraelectrodes for recording electrical potentials ("RTQs") while the smaller stars represent quadraelectrodes used for stimulating and/or lesioning ("STQs").

The invention provides a multichannel electrode ("MC electrode") which can record, stimulate and/or lesion upon a single insertion into a target site. The MC electrode according to the invention can be used for target localization and for acute or chronic neuromodulation therapy. The invention further provides interface connectors and cables for connecting the MC electrode to external units such as data acquisition and/or implantable source devices where part of a chronic monitoring and/or treatment regimen.

DEFINITIONS

The following definitions are provided for specific terms which are used in the following written description.

As used herein, "a multichannel electrode" refers to a non-planar backbone comprising a plurality of electrode channels disposed thereon, wherein at least one of said channels has an impedance suitable for recording an electrical signal from a cell and wherein at least one other channel has an impedance suitable for electrical stimulation of a cell.

As used herein, "flexible or semi-flexible" refers to an ability of a backbone to bend to an angle from 5°-45° relative to its longitudinal axis. Flexibility can vary depending on backbone length and diameter.

As used herein, a "light path" is a path through which light can pass from a light source to a target and/or from a target to a detector.

As used herein, "at least partially non-coplanar channels" refer to channels which lie at least partially on different planes, i.e., at least 5-50 µm of the length of each channel lies on different planes.

As used herein, a backbone which is "substantially cylindrical" refers to a non-planar backbone comprising a uniform diameter over at least 50% of its length.

As used herein, "a conical or frustoconical tip" refers to a tip comprising a base portion and a tip portion comprising a diameter which is smaller than the base portion (preferably at least two times smaller). A conical tip has a pointed tip end while a frustoconical tip has a flattened tip end.

As used herein, an "impedance suitable for recording" refers to an impedance which ranges from 200 kilo ohms to one megaohm, or greater As used herein, an "impedance which is suitable for stimulating and/or lesioning" refers to an impedance which is less than or equal to 200 kilo ohms.

As used herein, the term, "in communication with" refers to the ability of a system or component of a system to receive input data from another system or component of a system and to provide an output in response to the input data. "Output" may be in the form of data or may be in the form of an action taken by the system or component of the system.

As used herein, "coupled to" refers to a physical connection between one component of a system and another which can be direct or indirect.

As used herein, an electrode in "electrical proximity" to a cell refers to a distance which is sufficiently close to transmit electrical stimuli to the cell or receive electrical signals from the cell.

As used herein, a "known physiological property" refers to at least a property which is indicative of the normal functioning of a cell, such as an electrical activity which falls within normal limits of a normally electrically active cell (e.g., as determined by routine statistical testing using methods known in the art, setting confidence levels greater than or equal to 95%) or which is statistically significantly different from normal limits and which is associated with a disease state. The normal electrical activity of a cell will vary with the type of cell and can be determined empirically in a patient who exhibits normal responses to stimuli. In one aspect, "normal electrical activity" refers to voltages between 100 μV to 2 mV, and frequencies between 2 Hz and 200 Hz.

As used herein, "neural activity" refers to any physical behavior, output or phenotype of a neuron. For example, neural activity can be measured as one or more of the following parameters: action potential; depolarization; hyperpolarization; field potential; a behavior (e.g., motion, ability to respond to visual and/or auditory cues; a seizure); speech; sight; a product of a neuron (e.g., a hormone, growth factor, neurotransmitters, ions, and the like), etc.

As used herein, a "stimulus which activates a cell" is one which increases the power of the cell by at least two-fold or 50%. Power is calculated as the integral of the area under the curve of a recorded action potential and is inversely proportional to the distance of the MC electrode from the cell. Power also can be used to obtain an estimate of the distance of a signal source (e.g., one or more neurons) from the MC electrode.

As used herein, a "stimulus which inhibits a cell" is one which decreases an action potential by at least 50%.

As used herein, a "stimulus which permanently disables a cell" is one which permanently prevents a cell from generating an action potential. As used herein, an "acute treatment" is a treatment which lasts less than 24 hours.

As used herein, a "chronic treatment" is a treatment which lasts longer than 24 hours.

As used herein, "changing the amount of an agent provided to a target site" or "changing the amount of a drug provided to a target site" refers to an increase or decrease in concentration, bolus size, or flow rate provided to the target site.

As used herein, "normalizing electrical activity" refers to changing electrical activity to an amount of activity which is less than 10%, preferably, less than 5%, and still more preferably, less than 2.5% or 1% different from the activity defined for a normal cell, a normal population of cells, or normal cells in a population of normal individuals.

As used herein, a "detector" is a device capable of detecting one or more desired optical properties of an area of interest. Suitable optical detectors include any type of photon detector, such as photodiodes, photomultiplier tubes, cameras, video cameras, CCD cameras, and the like.

As used herein, "optical imaging" refers to the acquisition, comparison, processing and/or display of data representative of one or more optical properties of an area of interest. Optical imaging may involve acquisition processing and display of data in the form of images, but need not. For example, an optical image may be a display of spectral information acquired from a target site.

MC Electrode

In one aspect, an MC electrode according to the invention comprises a non-planar, backbone which comprises a plurality of electrode channels. Preferably, the backbone is a substantially cylindrical structure which is tapered at one end to form a substantially conical or frustoconical tip (see, e.g., as shown in FIG. 1) to facilitate its insertion at a site comprising one or more target cells (e.g., such as the brain, spinal cord, or a neural ganglia). Preferably, the outer diameter of the MC electrode (including backbone and channels) is less than 1.8 mm, preferably, less than 1.5 mm, still more preferably less than 1 mm, less than 0.8 mm, less than 0.7 mm, less than 0.6 mm, or less than 0.5 mm. The length of the electrode can vary depending on its application; however, in one aspect, the length of the MC electrode ranges from 5 mm to 10 cm. Preferably, the tip portion of the MC electrode is from about 0.05 to 4 mm.

In certain embodiments, the tip can comprise a radiopaque marker to facilitate localization of the position of the tip relative to one or more target cells. Radiopaque markers can be made from gold, tantalum, platinum, iridium material, and the like, which can be bonded to the tip using methods known in the art. In one aspect, the non-planar backbone of the MC electrode is a rod, fiber, or cable, which tapers at its end. Preferably, the backbone comprises a non-conductive material, such as glass, quartz, or a polymer or copolymer such as plastic, methacrylate, acrylate, polystyrene, polycarbonate, polyurethane, monovinylidene, PMMA, conducting polymers, polyimide, and the like. Less preferably, the backbone comprises a metal. In one aspect, the backbone is at least partially flexible, or semi-flexible (e.g., the backbone can bend to an angle of preferably 45° or less with respect to its or original longitudinal axis) to facilitate its use as a probe.

Figure 14A:
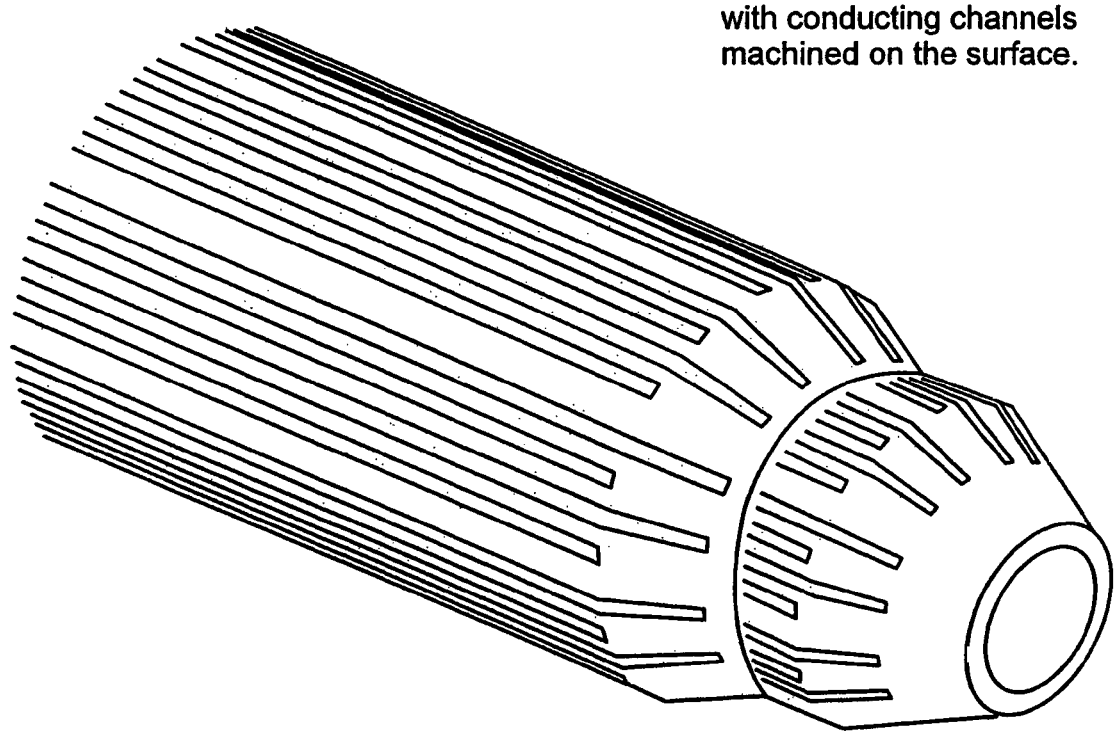
FIG. 14A shows an MC electrode according to one aspect of the invention, comprising a hollow backbone comprising a plurality of electrode channels. The lumen of the hollow backbone comprises a smaller backbone which can itself be hollow and which comprises additional channels disposed thereon.
Figure 14B:
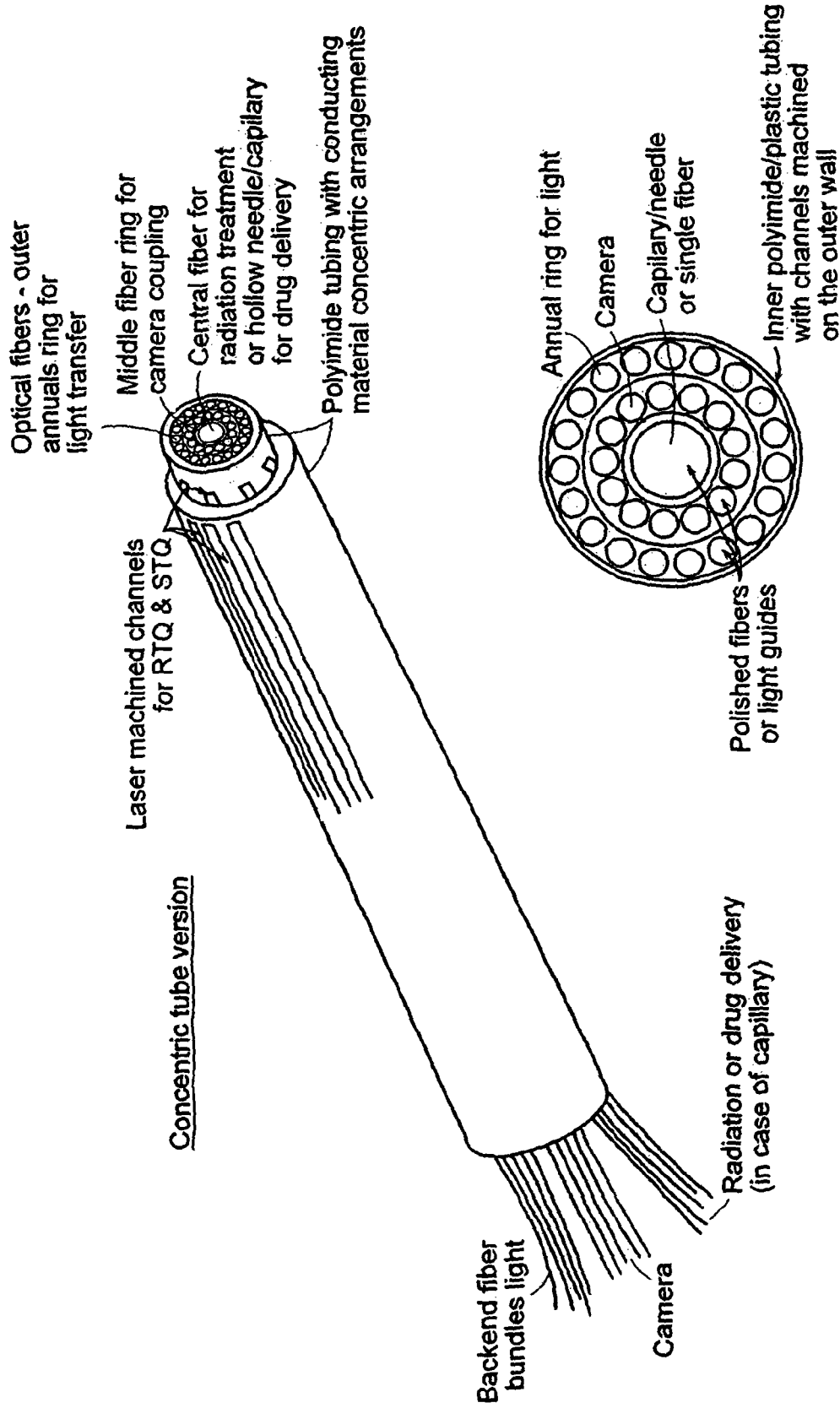
FIG. 14B shows an embodiment in which the smaller backbone comprises a plurality of optical fiber bundles and a central core which can be used to deliver radiation treatment or a drug to a target site.

In another aspect, the MC electrode comprises more than one backbone comprising channels. For example, as shown in FIGS. 14A and 14B, in one aspect, the MC electrode comprises a first hollow backbone into which a smaller, second backbone fits. Both the first and second backbone can comprise electrode channels, thereby maximizing the number of electrode channels that can be provided as part of the MC electrode. Preferably, fibers can be adjusted telemetrically to different lengths to record data at different distances and locations.

In a preferred aspect, the backbone provides an optical path through which light can be transmitted from a light source to a target site (e.g., a site comprising one or more neural cells) and through which light can be received from a target site. For example, the backbone can be a light guide or an optical fiber (e.g., such as a plated surgical grade optical fiber). In one aspect, therefore, the backbone comprises an optically transmissive core (e.g., having a refractive index of 1.41-1.62) surrounded by a cladding. The cladding facilitates light guiding by the core and also provides any necessary rigidity to the core. The materials of the cladding can vary, although the cladding also should be light transmissible. Preferably, the refractive index of the cladding is at least 0.5, at least 1, at least 2, at least 3, at least 5% less, or at least 10% less than the refractive index of the core. The cladding material should also adhere to the core material such that repeated flexing and bending of the backbone does not cause delamination at the interface between the core and cladding material. Preferably, the cladding is thermoplastic to withstand variations of temperatures during etching or micromachining of electrode channels onto the backbone.

In one aspect, the backbone is hollow and comprises the light path within its lumen. For example, one or more optical fibers or light guides as described above can be placed within the lumen (see, as shown in FIG. 14B). However, in another aspect, the backbone itself forms a hollow optical fiber. In this aspect, the backbone can comprise an inner hollow cylinder which functions as a core and which is surrounded by an outer cylindrical layer which functions as a cladding. In still other aspects, the backbone comprises a channel or groove on its outer surface into which an optical fiber or light guide can fit. The optical fiber or light guide in this embodiment can be used to receive optical information relating to the electrode itself, in addition to optical information relating to target cells in proximity to the electrode. For example, the optical fiber or light guide can be used to image the tip of the electrode when a radiopaque marker is affixed to it, to enable a user to more precisely determine the position of the electrode relative to one or more target cells.

The hollow portion of the backbone or a portion thereof which is not occupied by the light path can be used to supply fluids to a target site. In one aspect, a fluid is provided which comprises an agent such as a chemotherapeutic agent, radioactive agent, radiosensitizer, a trophic factor (e.g., a neurotrophic factor), antibiotic, hormone, steroid, growth factor, neurotransmitter, an agonist, or antagonist of a neurotransmitter, a symphathomimetic, a metabolite, cell (e.g., such as a stem cell), sedative, anti-epileptic (e.g., acetzolamide, amphetamine, carbamazepine, chloropromazine, clorazepate, dextroamphetamine, dimenhydrinate, ephedrin, divalproex, ethosuximide, magnesium sulfate, mephenytoin, metharbital, methsuximide, oxazepam, paraldehyde, pamethadione, phenacemide, phenobarbital, methsuximide, phenytoin, primidone, trimethadione, valproate, etc.), atherapeutic polypeptide and/or a nucleic acid encoding the same, an antibody which specifically recognize a tumor antigen, and combinations thereof.

Radiosensitizers include those agents which, when present during irradiation, enhance the cytotoxic effects of radiation, e.g., such as ionizing radiation. For example, the hypoxic radiosensitizer Misonidazole enhances the cytotoxic effect of X-ray and gamma ray radiation. 5'-bromo-2'-deoxyuridine (BUdR) or 5'-iodo-2'-deoxyuridine (IUdR) can be used to sensitize DNA to breakage by ionizing or ultraviolet radiation. Various heterocyclic compounds, in particular, those with oxidized nitrogen moieties, can be used for the purpose of radiosensitizing diseased cells such as tumor cells (see, e.g., Asquith et al., 1974, *Radiation Res.* 60: 108-118; Hall et al., 1978, *Brit. J. Cancer* 37: 567-569; Brown et al., 1980, *Radiation Res.* 82: 171-190; and U.S. Pat. No. 4,371,540), as can 1-substituted 3(5)-nitro-s-triazoles, quinoxaline-1,4-dioxide derivatives, diamines such as diaminetetrametronidazoles (DATMs) (see, e.g., U.S. Pat. No. 5,700,825), and texaphyrins (U.S. Pat. No. 5,622,946).

Chemotherapeutic agents include those chemical and biological agents such as peptides, proteins, lymphokines, antibodies, tumor necrosis factor, conjugates of antibodies with toxins, and other chemical or biological molecules which have an antitumor effect which is oxygen dependent. Chemotherapeutic agents include, but are not limited to: alkylating agents, such as Melphalan (PAM); Cyclophosphamide (CTX); cis-Diammminedichloroplatinum (II) (CDDP); nitrosoureas, such as N, N'-bis(II-chloroethyl)-N-nitrosourea (BCNU), nitrogen mustards; ethyleneimine compounds; alkyl sulphonates; cisplatin; dacarbazine; and the like. Antimetabolites, such as folic acid, purine or pyrimidine antagonists, 6-Mercaptopurine, 5-fluorouracil (5-FU), fluorodeoxyuridine, cytosine arabinoside, methotrexate and thioquinone also can serve as chemotherapeutics. Antibiotics including, but not limited to, actinomycin, daunorubicin, adriamycin and bleomycin and mitotic inhibitors, such as the vinca alkaloids (e.g., etoposide, vincristine and vinblastine and derivatives of podophyllotoxin) also can be used. Chemotherapeutic agents are described further in Gralla et al., 1984, *Cancer Treatment Reports* 68(1): 163-172. Mixtures of more than one chemotherapeutic or radiosensitizer agent also can be administered.

Toxins, such as neurotoxins, also can be delivered to a target site, for example, when it is desirable to eliminate malfunctioning cells. Preferably, the agent is selected to supplement the effects of electrical stimulation (i.e., whether to activate or inhibit the activity of cell(s)).

A fluid also may be delivered and used to irrigate a site being treated and may comprise physiological saline. Alternatively, or additionally, the fluid may comprise a radiopaque agent or contrast agent (e.g., such as barium sulfate), for use in localizing the position of the MC electrode tip relative to cells at a target site.

Imaging agents also can be delivered, such as lanthanide metal complexes comprising gadolinium, samarium or ytterbium, as well as metals known to exhibit similar chemistry such as yttrium, indium and gallium. Radioactive tracer molecules also can be used.

Preferably, the end of the backbone distal from the tip is in communication with a pump which provides sufficient pressure to deliver the fluid to the target site. The operation of the pump can be manually controlled by a user or can be controlled via instructions programmed into a processor in communication with both the pump and the MC electrode. Alternatively, or additionally, the pump can be provided with a microprocessor for providing instructions to the pump.

Preferably, the backbone of the MC electrode further comprises an electrically conductive layer onto which a plurality of electrode channels are disposed (e.g., by micromachining, described further below). The electrically conductive layer can comprise metal such as gold, copper, nickel, titanium, platinum, silver, silver-plated copper, silver tungsten, silver cadmium-oxide, silver tin-oxide, indium-tin-oxide, tin-oxide, and the like. The electrically conductive material can be bonded to the backbone using an adhesive undercoating, such as nickel/titanium. In a particularly preferred embodiment, a coating is used which is substantially transparent, yet still conductive, such as indium-tin oxide, or tin oxide. For example, this may be desirable to allow an MC electrode which comprises a light path to transmit light along its length as well as at its tip.

The conductive material comprises a plurality of electrode channels. Preferably, the plurality of electrode channels are organized into sets of channels, each set comprising at least two, and preferably, at least four channels. Each set is separated from the other by a region of insulating material such that there is no electrical cross-talk between sets of channels. The insulating material may include, for example, any material having a dielectric constant greater than that of the electrode channel metal, and materials, such as glass fiber, silicon elastomers, or like material, having a high dielectric constant can be used. In one aspect, substantially all of the channels also are covered by insulating material except for region(s) at the tip (e.g., of about 2 to 5 µm) to provide "open contacts" or surfaces through which electrical current can pass and be received. In a currently preferred embodiment, the MC electrode is coated with an insulating material such as polyimide or Teflon® to isolate individual channels and enhance the biocompatibility of the electrode (e.g., to reduce biological rejection/inflammatory responses). Coating thickness can vary so long as the proper/desired amount of insulation is obtained.

Each set of channels performs a specific function such as recording or stimulating/lesioning. Preferably, the MC electrode comprises at least one set of channels for recording ("a recording channel set") and at least one set of channels for stimulating and/or lesioning ("stimulating/lesioning channel set"). Still more preferably, a plurality (i.e., at least two) of recording channel sets and stimulating/lesioning channel sets are provided. Recording and stimulating can be performed sequentially according to a user's preference as described further below.

The overall diameter of the MC electrode will ultimately depend on the number of and spacing of channels which are placed on the non-planar backbone, the spacing between sets of channels and the width of individual channels. These parameters in turn depend on the desired use for the MC electrode. For example, the tip size determines the ability of the MC electrode to resolve separate signal sources (e.g., neurons) and to obtain electronic signatures of one or more cells, while the channel width determines the electrical properties of the channel (e.g., its ability to stimulate or record).

The lower limit on channel size is generally the lower limit on the size of a cell or group of cells to be stimulated or whose action potentials are to be recorded, and, generally, the size of the electrode channel tip, or open contact surface, should be at least ½ to ⅓ of the size of the cell. A typical neuron generally is on the order of 10 µm to 100 µm and therefore, in one aspect, a lower limit on channel tip or open contact surface size may be set at greater from an amount greater than 0 to 10 µm in width. This is particularly desirably, when the channel is part of a recording channel set for obtaining high-resolution data from single neurons. However, it may be less desirable to provide stimulating electrodes which can only stimulate single neurons at a time, and therefore the channels at the tip or open contact surface in stimulating/lesioning sets are preferably larger than 10 µm, i.e., on the order of 11-30 µm and preferably, 20-30 µm in width.

Generally, whether a recording channel set or stimulating channel set functions to record or stimulate, respectively, depends on the impedance of the set. Impedance is a measure of a material's resistance to carrying an electrical current and can be controlled at least in part by controlling the dimensions of the channels, as described above. For example, recording channel sets have a high input impedance (greater than or equal to 200 kilo ohms to 1 megaohm) as a result of the small diameters of their channels while stimulating channel sets have lower impedance (less than 200 kilo ohms) as a result of their larger channel cross section. Impedance further can be modulated by providing microresistors in communication with the sets of channels at an end of the electrode distal to the tip (i.e., as part of the interfacing connector described further below). The ratio between exposed and insulated regions of the channels also affects impedance during use. Generally, the larger an exposed region is compared to an insulated region, the lower the impedance value which can be expected. Impedances can be measured and optimized as is routine in the art, e.g., by obtaining measurements in phosphate buffered saline using an HP 4194A Gain/Phase analyzer or other impedance measuring device Generally, a recording channel set cannot be used effectively to stimulate (except to micro-stimulate or to stimulate an evoked action potential for recording purposes) and a stimulating channel set cannot be used effectively to record. However, a stimulating channel set also can be used to lesion, the difference being that stimulating (e.g., to activate or inhibit a neuron) is reversible while lesioning (e.g., to disable a neuron is not). Electrical discharges of relatively low frequency (e.g., about 50 Hz) are expected to excite nearby neural cells while those of relatively high frequency (e.g., about 200 Hz) are expected to inhibit nearby neural cells. Repeated high frequency stimulation is expected to permanently disable or lesion a neural cell.

The ability to stimulate or lesion is dependent on the current and frequency of the electrical discharge through the stimulating/lesioning channel set. Stimulation generally requires low current (microamps) and frequencies of up to about 200 Hz, while lesioning generally requires high currents of up to 2 milliamps with frequencies up to about 200 Hz. Frequency can be continuous or pulsatile.

In one aspect, a set of electrode channels is used to provide an RF signal via connection to an RF output source and the RF signal is provided at a frequency which can permanently disable a cell. See, e.g., as described in U.S. Pat. No. 6,259,952. The RF output source can be coupled to one or more sets of electrode channels by means of the interfacing connector described further below.

By providing more recording and stimulating sets which can be used selectively (e.g., according to instructions from a processor in communication with the MC electrode via an interfacing connector, discussed further below), the user has greater probability of successfully localizing target cell(s) (e.g., one or more diseased neurons) and treating these (e.g., activating or inhibiting, or disabling, i.e., lesioning) while minimizing the need to remove and re-insert the MC electrode. In a particularly preferred embodiment, there are 20-50 sets of four channels per set per a 0.5 mm diameter fiber. In one aspect, for example when the backbone is hollow, a smaller diameter MC electrode may be fitted into the lumen of a larger MC electrode, providing still more sets of channels (see, e.g., as shown in FIG. 14A). The smaller diameter electrode can comprise a light path for transmitting light (e.g., the backbone of the smaller diameter electrode can be a light guide or optical fiber or can provide another functionality such as a conduit for fluid delivery) (see, e.g., FIG. 14B).

Figure 2:
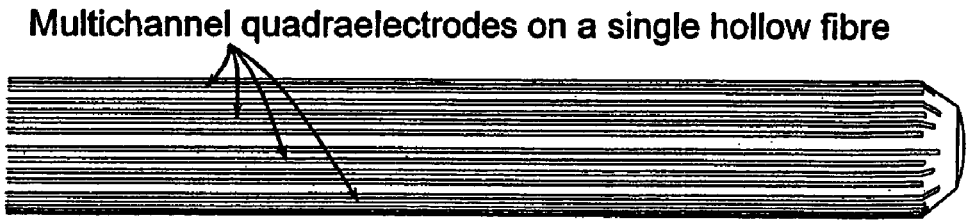
FIG. 2 shows an MC electrode comprising an optical fiber backbone with multiple alternating RTQs and STQs.

The multiple channels of the MC electrode can be located strategically on the fiber (see FIGS. 1 and 2) to maximize signal resolution by recording electrodes and the range of a target site (e.g., size, number of cells) that can be stimulated/lesioned. In a currently preferred embodiment, a group of four geometrically arranged channels is provided, forming a "quadraelectrode". At least two of the set of four channels lie at least partially in a different plane (e.g., at least at the tip) and preferably, two of the set lie in the same plane (see, e.g., as shown in FIG. 1). In another aspect, at least three electrode channels lie on a single plane and the fourth electrode lies at least partially on a different plane (e.g., at least at the tip). This non-coplanar arrangement gives the best resolution of neuronal signals in three-dimensional space. As can be seen in FIG. 1, channel lines can be staggered and at least one channel line placed in a geometrically different plane to meet this non-coplanar criteria.

Other designs and variations of electrode tip geometries also are possible which will maintain an at least partially non-coplanar configuration of at least two electrode channels. Other arrangements and modifications may include a precisely telescoped arrangement of two fibers with sets of channels divided between the inner and outer fibers and a single fiber with serially micro-machined notches along its shaft that will allow placement of the fourth electrode in a non-planar arrangement. The concentric tube within a tube arrangement shown in FIGS. 14A and 14B also can be used to create a non-coplanar arrangement of channels. FIG. 14B shows a scenario in which at least one channel of a set is on the first hollow backbone and at least one other channel of the set is on the second smaller backbone within the lumen of the first hollow backbone.

For example, in one aspect, two hollow polyimide tubes, each pre-coated or layer with a conducting material are provided. One tube fits within the hollow lumen of the other and recording channel sets and stimulating sets are distributed on the tubes such that two channels of one set are on one tube and two are on the other tube, or three of the channels are on one tube and one channel is on the other tube. This configuration maximizes the number of recording channel sets and stimulating channel sets that are part of the MC electrode. The central core of the innermost tube additionally can house one or more fibers that have no electrode channels but which can be used as a light path or as a delivery device to deliver one or more therapeutic agents (e.g., drugs, radioactive agents, chemotherapeutic agents, and the like).

A similar configuration can be obtained by providing a planar sheet of polyimide or other flexible material coated with a conducting material and wrapping one or more of the sheets around a cylindrical shaft (e.g., a tube or fiber) or simply rolling the sheet(s) to create a multilayered structure comprising two or more backbones for electrode channels. One or more light paths can be created in a central hollow lumen. For example, one or more optical fibers can be placed within the central hollow lumen. Additionally, or alternatively, one or more hollow fibers can be inserted into the central lumen to provide a conduit for delivery of one or more therapeutic agents, as described above.

In a currently preferred aspect, the MC electrode according to the invention has at least two types of quadraelectrodes. A "recording type quadraelectrode" (RTQ) preferably has high input impedance to record the action potential of cells (e.g., such as neuronal signals) and to deliver micro-stimulation. Preferably, the geometry of channels at the tip of the MC electrode is orthogonal to the longitudinal axis of the fiber so that the cross-sectional planes of the electrode tips are perpendicular to the optical axis of the fiber with the separation spacing between individual tips being in the range of 5 to 50 µm or more, and preferably being between 5-30 µm. In one aspect, the separation between each of the four channels in the RTQ ranges from 2-10 µm so that incoming signal will be registered by the four channels of the RTQ virtually simultaneously to provide four different electrical views of the same signal. This allows localization of a signal-generating neuron in three-dimensions, which is crucial for the identification of target cell(s).

Preferably, by recording from all four channels simultaneously, the RTQ provides electronic signature or electronic "image" of one or more neurons in proximity to the RTQ to allow the precise localization of the one or more neurons. In one aspect, the MC electrode records signals from neurons 20 to 100 µm away from the tip of the MC electrode, enabling the electrode to record signals from up to 8-10 cells per RTQ.

Because data from all channels within an RTQ set are captured simultaneously, an electronic signature can be obtained for one or more cells, providing "a physiological image" of the one or more cells. This allows a user to produce a local functional map representing the activity of cells (e.g., such as neurons) within a particular region of tissue being evaluated. For example, the geometry of channels at the tip of the MC electrode enables a user (e.g., via a processor in communication with the electrode) to estimate the distance of one or more cells from the tip of the electrode, enabling a user to define the functional geometry of tissue being evaluated with the MC electrode. This functional map can be correlated with an optical image obtained from an MC electrode comprising one or more light paths, light focusing elements and/or cameras, as described above, and can be further correlated with symptoms of the patient.

A "stimulating type quadraelectrode" (STQ) has relatively low impedance to pass currents intermittently and preferably, to stimulate more than one neuron at a time. The separation between each of the four channels of the STQ is typically approximately 5 to 30 µm wide. The current used to stimulate typically ranges from 100-500 µA, while voltage preferably ranges from 1-5V.

Generally, STQs comprise at least one channel with a positive polarity and at least one channel with a negative polarity. Combinations of three positive channels and one negative channel, three negative channels and one positive channel, or two negative channels and two positive channels can be provided.

It should be obvious to those of skill in the art that MC electrodes according to the invention can have variable specifications with regards to the fiber type, conductive material coating thickness, electrode surface area and its current carrying capacity with respect to the electrode geometry and feature size and size of channels. Variations can be optimized and can be tested as in Example 1, below, and are encompassed within the scope of the invention.

Probe Housing

Figure 4:
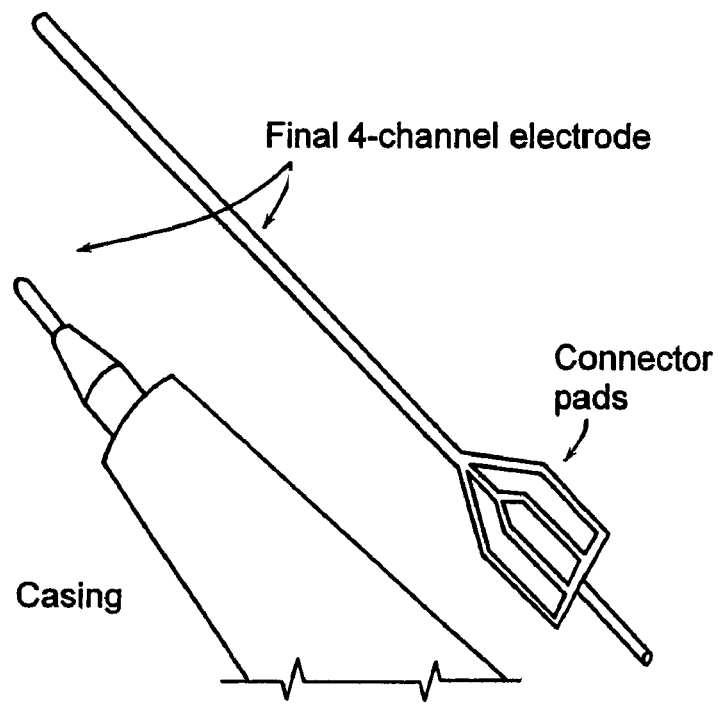
FIG. 4 shows an aspect of the invention in which the MC electrode comprises a cylindrical metal rod which is covered by a machined gold-plated copper flex circuit board onto which channels are etched.

In one aspect, the MC electrode is at least partially contained within a probe housing or casing to facilitate its handling. Preferably, as shown in FIG. 4, at least a tip portion of the MC electrode extends from a tapered end of the probe housing. The probe housing generally is made of a biocompatible, sterilizable material and further can comprise one or more activating buttons connected to switches coupled to the interfacing connector, for example, which can be used to activate one or more functions of the electrode (e.g., stimulating/lesioning, recording, imaging, drug delivery, and the like). The probe housing itself may comprise multiple functionalities, e.g., such as fluid delivery dispensers, cameras affixed thereto, and the like, and in one aspect, the probe housing is removable from the MC electrode.

The probe housing also can comprise one or more radiopaque markers. This may be useful, for example, when an electrode tip, also comprising a radiopaque marker, is advanced or retracted or rotated within the probe housing, enabling a user to judge the relative amount of movement of the tip as the distance between a radiopaque marker on the tip and on the probe housing changes.

Multiple MC electrodes also can be provided within a single probe housing and preferably, the movement of each of the electrodes can be independently controlled, e.g., by providing each electrode with its own interfacing connector as described further below.

Engineering the MC Electrode

In one aspect, the invention provides a method of producing an MC electrode. Preferably, the method comprises obtaining a non-planar backbone material which is substantially cylindrical, e.g., such as a rod, a wire, a fiber, a cable, and which comprises a first and second end. The first end is substantially flattened while the second end preferably tapers to a tip. The tip portion of the backbone can be conical or frustoconical (e.g., having a flattened end). A tip also can be fabricated from a backbone which is substantially entirely cylindrical and chamfered at the end. A tapered tip also can be produced using a support structure to maintain the position of the backbone while the second end of the backbone is grounded and polished to a tip (see, e.g., as described in U.S. Pat. No. 6,257,971). When the backbone comprises an optical fiber, the tip can be ground into a convex surface to create a focussing lens to enhance the imaging capabilities of the electrode.

In a particularly preferred aspect, the non-planar backbone is an optical fiber. Optical fibers are commercially available (see, e.g., Corning® optical fibers, at www.corning.com/opticalfiber) but also can be manufactured using methods known in the art. See, e.g., as described in U.S. Pat. Nos. 6,243,520; 5,829,445; 5,755,850; 4,828,359, for example. Polyimide tubing also can be used as can sheets of flexible material which can be rolled to create the concentric tube structures described above.

As discussed above, the length and diameter of the backbone generally can be varied from 5 mm to 10 cm in length and from 1.8 mm in diameter, to less than 0.6 mm in diameter, and including less than or equal to 0.5 mm in diameter. In one aspect, a backbone greater than 10 cm in length is selected and cut to an appropriate size (e.g., by a laser or fiber cutter).

In a preferred aspect, an adhesive coating of a conducting or non-conducting material is layered onto the backbone, e.g., by dipping, immersion, thin or thick film deposition, electroplating, electrochemical plating, and the like. Preferably, the layer of non-conducting material ranges from 1 to 10 μm thick. If a non-conducting material is deposited, then an electrically conductive material is next layered onto the adhesive coating (e.g., by electrodeposition, sputtering, and the like), preferably, within less than a minute after placing the adhesive coating on the non-planar backbone. The layer of conductive material ranges from 1 to 20 μm thick and must provide a sufficiently uniform coating to transmit an electrical signal from the second end of the MC electrode (e.g., the tip) to the first end of the MC electrode (e.g., the end proximal to the interfacing connector).

To produce channels on the coated backbone, an improved laser micro-machining technology was developed. Ultra precision laser machining has emerged as an attractive tool for processing a myriad of materials in various industrial fields and in medicine (Ogura et al., 1998, *Laser Focus World* 34: 117-18 and 120-3; Gower, "Industrial Applications of Pulsed Laser Micromachining," *Proc. of the 1998 International Symposium on Information Theory, CLEO/EUROPE'98*; Nikumb and Islam, "Precision Machining of Ceramics and Metals for Manufacturing Applications," *CAP Congress on Laser Material Processing and Industrial Applications*, University of Waterloo, Jun. 14-17, 1997). This development is mainly due to the rapid progress in the design of diode pumped solid-state lasers (see, e.g., Petersen and Nighan, "A High Power, Diode-Pumped Solid State 355 Nm Laser System For Micromachining Applications," *Conference on Lasers and Electro Optics CLEO-Technical Digest* 1998; Nikumb et al., "Precision Machining Of Thin Metal Foils Using A Diode Pumped Solid State (DPSS) Laser," *Proceedings of the 17th International Congress on Applications of Lasers and Electro-Optics, ICALEO 98*, Orlando, Fla., USA, Nov. 16-19, 1998). These lasers produce powerful light impulses with duration ranging from a few nanoseconds ($10^{-9}$ s) to femtoseconds ($10^{-15}$ s) (see, e.g., Kruger and Kautek, 1999, *Laser Physics* 9: 30-40; Chang et al., 1998, *J. of Laser Applications* 10: 285-91; Nikumb and Islam, "Material Removal And Precision Machining Of Ceramics Using ND:YAG Lasers," *14th International Congress on Applications of Lasers and Electro-Optics 95 (ICALEO 95)*, San Diego, Calif., USA, Nov. 13-16, 1995, 168-77). Laser devices are now used in thin film synthesis, material processing, micro-fabrication, electronics, and biomedical and opto-electronics areas (see, e.g., Nikumb and Islam, "Precision Machining Of Ceramics And Metals For Industrial Applications," *Canadian Association of Physicist (CAP)* Conference, Waterloo, Ontario, June 1998).

Therefore, in one aspect, a laser beam is tightly focussed to a near diffraction limited spot size and is used to machine channels of the desired length and depth in the electrically conductive coating material layered onto the MC electrode backbone. Because the amount of heating is minimized by using a short pulse laser, backbone materials and their coatings can be machined with ultra-fine accuracy.

Channel dimensions less than a few microns can be achieved with precise control of work piece motion and proper choice of laser beam and factors which affect the proper choice of laser beams are known in the art and described in Bordatchev and Nikumb, "Dynamic Calibration Of Motion System For Laser Micro-Machining," *NRC Research and Technology Development Forum Magog*, Quebec, Mar. 3-5, 1999, for example. Additionally, the machined depth and the surface finish of a machined area (e.g., such as a channel) can be controlled within the high tolerance values. Superfine microfeatures can be produced on complex, multi-layered materials (e.g., such as optical fibers) using an integrated, computer-controlled, multi-wavelength, multi-axis laser precision machining system as described in Zhou et al., 1995, "Sensors For Intelligent Machining—A Research And Application Survey," *Proceedings of 1995 IEEE Conference on Systems, Man and Cybernetics*, Vancouver, British Columbia, Canada, Oct. 22-25, 1995; Nikumb and Islam, 1997, "Laser Depth Controlled Precision Machining Of Advanced Ceramics," *LASE '97*, San Jose, Calif., February 1997, *Proceedings of SPIE. Laser Applications in Microelectronic and Optoelectronic Manufacturing II (abstract 2991) SPIE:* 176-82; and Nikumb and Islam, 1996, "Depth Controlled Precision Machining Of Structural Ceramics Using Nd:YAG Lasers," *Canadian Association of Physicists (CAP) Congress on Laser Material Processing and Industrial Applications*, Ottawa, Ontario, Jun. 16-19, 1996, for example.

In one aspect, laser machining of channels and generation of particular tip geometries is performed using the Master CAM package (available from In-house Solutions, Ontario). To achieve a high degree of accuracy with laser micromachining, a fiber holding device is used in which the movement of the main body of the electrode is controlled using rotational drives that are capable of rotational movement to within ±10 nanometers. Preferably, a closed loop, camera-based vision system (e.g., a coordinate measuring machine or CMM and sensing devices) with inspection-metrology software enables close monitoring and control of channel dimensions and connector feature sizes to within designed specifications; e.g., as described above. Such systems are known in the art and available from Optical Gaging Products Inc. (OGP, Rochester, N.Y.); The L.S. Starrett Co. (Athol, Mass.); and Mitutoyo America Corp. (Aurora, Ill.). See, also, as described in Bloemhof et al., 2000, *Porch. SIP* 4007: 889-898. Such systems are available from Aerotech, Penn., and Dover Instruments Corporation, Massachusetts, for example. In a preferred aspect, once channels are machined on the substantially cylindrical body of the backbone and at the tip (as shown in FIG. 1), the electrode is at least partially coated with an insulating material, such as polyimide or Teflon®. Minimally, the spaces between sets of electrode channels should be coated to prevent cross talk between sets of channels. However, in one aspect, substantially all of the electrode is coated except for the tip or a portion of the tip region of the electrode to provide at least a surface of the electrode channels ("contact point") exposed to provide stimuli to, or to receive action potentials from, a target site. If the entire fiber is coated, then further micromachining of contact point(s) is performed on the coated fiber. Small beam lasers are then used to open specified areas on the channels as to create "open contact regions". Portions of the MC electrode also can be selectively coated with an insulating material using a mask.

As a final step, the MC electrode is interfaced with an interfacing connector described further below.

Interfacing Connector

In one aspect, an interfacing connector is provided to couple the MC electrode to various external devices and/or to modulate the function of the MC electrode. In a simple example, as shown in FIG. 4, an interfacing connector can comprise a plurality of wires or leads, each wire or lead connected to a channel at one end (shown in Figure) and connectable to at least one external system at another end. For example, the wires/leads can be mounted and electrically connected to PC boards using ultrasonic bonding, wire bonding, laser joining or laser soldering techniques, as is known in the art, and exposed connections can be stabilized or insulated with epoxy or another insulating material. The pins on the PC board then can be mated directly to standard integrated circuit sockets (e.g., such as DIP sockets) permitting easy handling and connection (e.g., to preamplifiers and/or microdrives and/ or processors, etc.).

In another aspect, a connector is provided which comprises a support which holds an array of mating conductor pins (see, e.g., U.S. Pat. No. 4,869,255), for making contact with each of the individual channels of the MC electrode. A connector with spring-loaded contact pins is described in U.S. Pat. No. 5,560,358.

Figure 3:
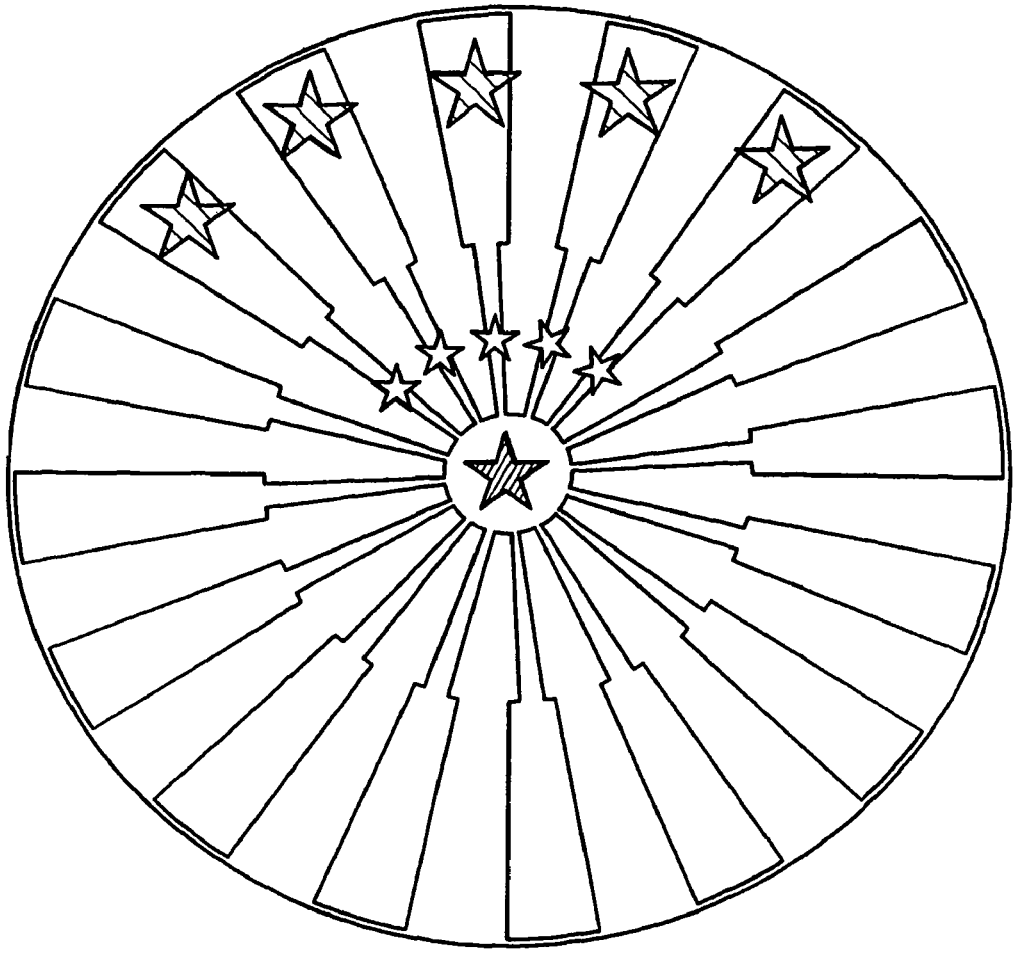
FIG. 3 is a schematic of an interfacing connector according to one aspect of the invention for connecting an MC electrode to a data acquisition system and to a drive for activating and controlling the motion of the electrode. The center of the connector is for connecting to the MC electrode. The connector comprises a contact point for each channel on the MC electrode. Ultrathin wires are used to connect a drive to the MC electrode.

Preferably, the interfacing connector enables connection to a plurality of external devices and can comprise additional functionalities for modulating the function of the electrode. FIG. 3 shows a cross-section through an interfacing connector according to a currently preferred embodiment. As shown in FIG. 3, in one aspect, the connector is a generally cylindrical unit comprises a housing with an inner wall 1 and an outer wall 2 and having a first and second end (not shown). Preferably, the diameter of the connector housing is relatively small (5 mm or less) so that at least a portion of it can be tunneled underneath a patient's skin from an incision site to an external exit site. The first end of the interfacing connector is proximal to the first end of the MC electrode (e.g., the end distal to the tip portion), while the second end of the interfacing connector is coupleable to at least one external device (e.g., such as a drive for controlling the movement of the MC electrode).

The inner wall 1 of the interfacing connector defines a central opening into which the first end of the MC electrode is placed. Preferably, the opening is only slightly larger than the diameter of the first end of the MC electrode so that the electrode fits tightly within the opening (e.g., does not freely rotate unless manually forced to do so) and can form electrical contacts with each of a plurality of central terminals 3 which extend from the outer wall 1 to form the inner wall 2. The central terminals can be fabricated using a laser micromachining process.

Each central terminal 3 is fused to the longitudinal section of the device at the outer wall 1 and makes electrical contact with a channel in the MC electrode at least one point along the channel. Preferably, the portion of the central terminal 3 which contacts the channel is bonded to the channel and the portion of the central terminal 3 which contacts the outer wall is bonded or soldered to the outer wall. To join the connector to the main MC electrode body, perfect alignment with respect to each channel line must be maintained. In one aspect, a device which permits indexed rotation of the entire electrode-connector assembly along a guide plate holder is used.

The connections between the MC electrode and the interfacing connector have different impedance depending the function of the channel (e.g., whether the channel is part of a recording channel set, such as an RTQ, or a stimulating/ lesioning channel set, such as an STQ). The input impedance of every channel can be changed at will (for example, during an acute treatment procedure) by using variable micro-resistors on the connector.

Standard or layered materials known in the art of electronics (e.g., vs. biocompatible materials) can be used for electrical connection and in the bonding/soldering process since this part of the device is not in direct contact with the tissue area. For example, epoxy can be used as an insulating material in this portion of the device.

Preferably, as described above, the connector is interfaced at its second end to at least one external device. External devices within the scope of the invention, include, but are not limited to a drive or microdrive device, a processor (e.g., comprising a data acquisition system), a light source, an oscilloscope, a detector, a fluid delivery pump, a suction device, an amplifier (e.g., a multichannel amplifier), filters, a power supply, and the like. External devices also can be provided within the interface housing and coupled to the MC electrode via the central terminals 3 of the interface connector. These devices can be used to activate, disrupt, or otherwise modulate signals received or transmitted by the MC electrodes. Preferably, individual sets of channels can be controlled independently of other sets (e.g., RTQs can be controlled independently of STQs, and individual RTQs and STQs can be controlled independently of each other). For example, amplifiers, filters, and/or microresistors, as described above, can be provided within the interface housing.

Figure 15:
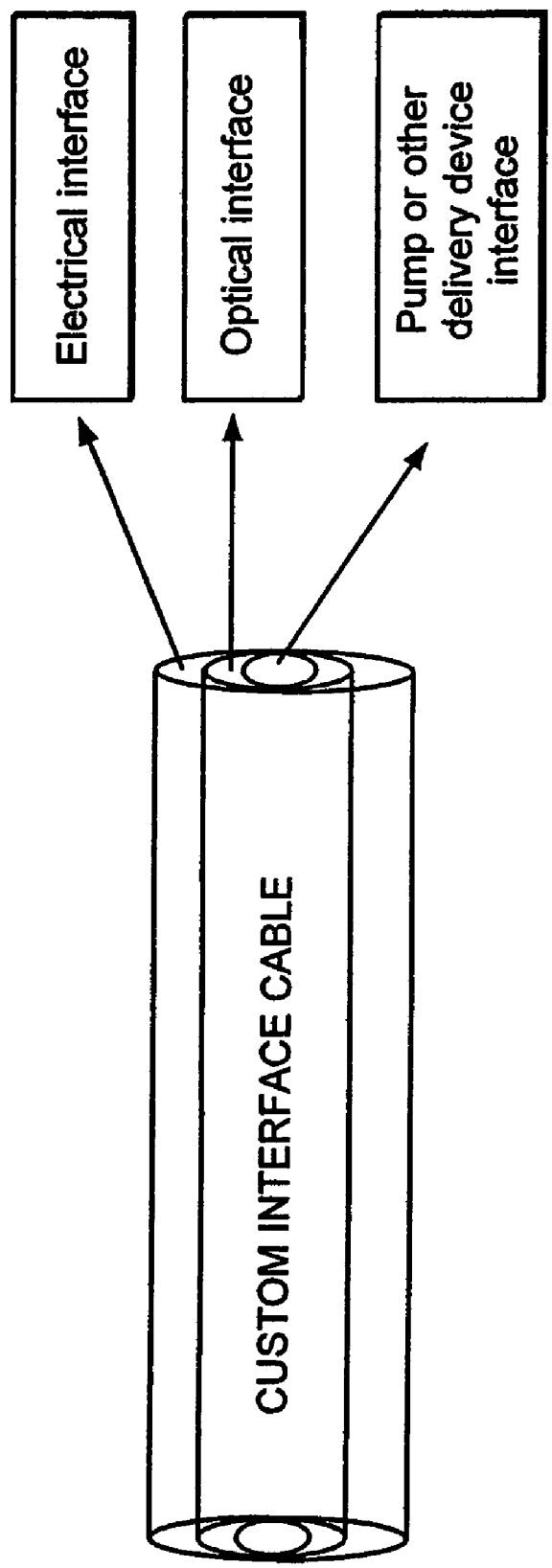
FIG. 15 is a schematic showing an interfacing cable according to one aspect of the invention for interfacing the interfacing connector (and through it the MC electrode) to one or more external systems.
Figure 16:
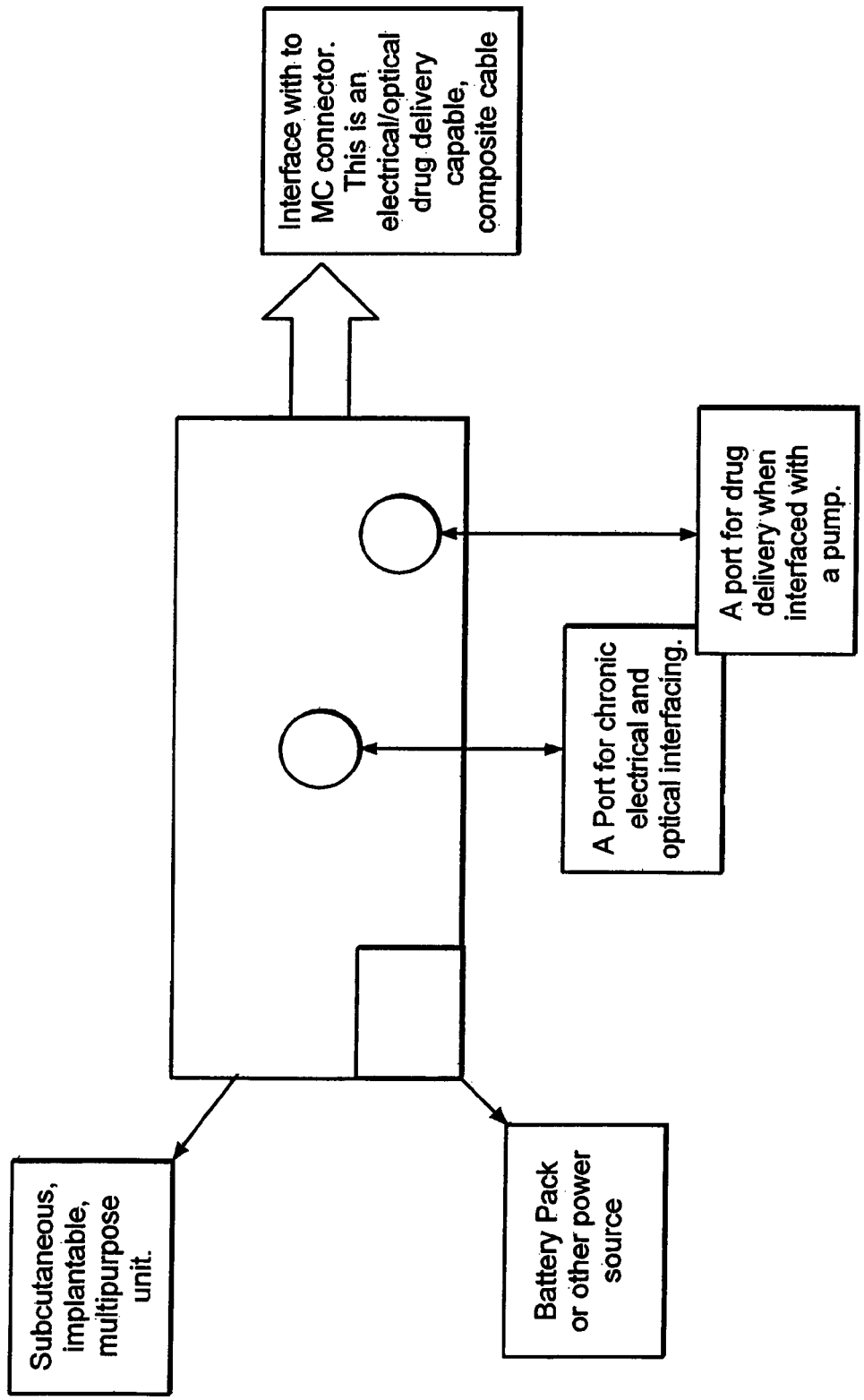
FIG. 16 is a schematic illustrating the multiple functions of an MC electrode.

In one aspect, the interfacing connector couples to the various external devices or systems through an interfacing cable such as the one shown in FIG. 15. The interfacing cable can comprise a plurality of concentric tubes for connecting with the electrical components of the interfacing connector, the optical interface(s) of the interfacing connector, and the portion of the interfacing device which is coupled to the delivery device or passage of the MC electrode. Preferably, the cable is flexible and interfaces with the interfacing connector in such a way that it provides electrical connectivity, optical interfacing for imaging, and can modulate the delivery of agents, fluids, radiation, radiowaves, and the like, through the MC electrode (e.g., via a pump, as described further below).

More preferably, the cable provides a mechanism for registering and storing or buffering electrical data (e.g., such as neuronal data) and can transmit this data on demand (e.g., in a serialized fashion) to a data acquisition system as described further below. This enables the device to maximize the amount of useful information which can be obtained simultaneously from multiple channels of the electrode. Still more preferably, the cable is designed to be connectable to a plurality of MC electrodes via their individual interfacing connectors. In one aspect, when the MC electrode is part of a chronic treatment regimen, the cable is used to connect the MC electrode to an implantable source device stimulating and recording device described further below.

External Devices

Microdrives

Preferably, the connector is interfaced with a drive unit (e.g., such as a microdrive) for controlling the motion and/or advancement of the MC electrode through a tissue (e.g., such as the brain, spinal cord, or a neural ganglion) to a target site. Many microdrive devices have been developed for use in laboratory animals (e.g., FHC microTargeting Drive®, available from FHC, Inc., Bowdoinham Mass.). Radionics (Burlington, Mass.) supplies commercially available microdrives (e.g., such as the AccuDrive™ drive) suitable for use in human subjects.

Preferably, the microdrive provides easy setting of zero points with reference to a patient's scalp, skull, or dura, for example, and comprises a carrier unit for receiving the interfacing connector and an adaptor for placing the drive and electrode in a stereotactic frame, which keeps the MC electrode stationary relative to a patient into which the electrode is inserted. Preferably, the frame is compatible with performing analyses by CT, MRI, or a tomographic scanner. In one aspect, the frame also is coupled to a camera apparatus which can obtain optical information from a surgical field and which can correlate the information to data relating to the patient's anatomy (e.g., such as obtained by CT and/or MRI), enabling more accurate positioning of the MC electrode. See, e.g., as described in U.S. Pat. No. 6,275,725.

In another aspect, the drive unit is coupled to a sleeve or telescoping cannula into which the interfacing connector and at least a portion of the electrode fits and which can function as a probe housing to protect the electrode from damage. The drive unit can comprise control elements, for example, advancement knobs, or knobs which control movement of the probe along an x-, y- or z-axis relative to the stereotactic frame.

However, the drive system also can be coupled to a three-dimensional digitizer probe and one or more mechanically articulated arms as in frameless stereotaxy (see, e.g., as described in U.S. Pat. No. 6,120,465). For example, a scan of the patient's head may be obtained, and a set of two-dimensional (2-D) scan slices can be collected and inputted into a computer graphic workstation in communication with a processor which in turn is in communication with the MC electrode, interfacing connector and drive. The workstation can assemble the 2-D scan slices and display a three-dimensional representation of the patient's anatomy (e.g., providing an image of the patient's brain). The digitizer probe has an encoding mechanism to provide data relating to its position in space back to the processor, so that when the probe tip is pointed to part of the patient's anatomy, the position of the tip relative to the three-dimensional representation can be determined. In this way mapping between physical and graphic space can be performed and used to guide the movement of the electrode. In one aspect, the digitizer is a part of a probe housing which contains the MC electrode.

Connections between every channel from the MC electrode connector onto individual contact pins on the drive can be accomplished by point soldering or silver-plating individual wires from the MC electrode connector onto the pins of a drive connector (e.g., the portion of the drive for receiving the interfacing connector). Preferably, the drive connector is connected or connectable to a processor which can provide instructions to the drive unit to control the movement of the MC electrode in response to signal measurements (e.g., obtained from one or more recording channel sets or RTQs).

In a chronic treatment regimen, a miniaturized microdrive that can advance and retract the MC electrode in small amounts is incorporated into the interfacing device which is implanted subcutaneously. Preferably, the microdrive also permits rotational movement of the MC electrode; in this embodiment, the pins of the drive connector also would have to be capable of rotational movement. The interfacing device can further house recording and stimulating circuitry as described further below.

Amplifiers and Preamplifiers

The MC electrode can be coupled to amplifiers, which are either external to the interface connector or which are placed within the interfacing connector housing. Use of an appropriate amplifier may be critical to maximize signal quality from the small, high impedance sites on the MC electrode (e.g., such as from recording channel sets or RTQs). Preferably, amplifier gain is 10-100, and more preferably from 10 to 1000 times, the signal obtained from the MC electrode. Preferably, amplifiers have built-in common mode rejection. Amplifier circuits also can have bandpass filters and even A-D converters microfabricated onto their contacts. Preferably, these are all shielded from a patient within the interfacing device.

In one aspect, the MC electrode is coupled to a microchip which comprises multichannel amplifiers, multiplexing circuitry and, optionally, an RF transmitter (see, e.g., as described in U.S. Pat. No. 6,171,239) and which is placed within the interfacing connector housing. Preferably, an amplifier is connected to at least each recording channel set (e.g., such as an RTQ), and more preferably, to each channel of each recording channel set. The microchip can be attached to coils permitting power to be transmitted to the MC electrode via an external power source and enabling transmission of multiplexed, multichannel neural signals out of the MC electrode as a serial data stream. The external power unit further can comprise a power coil and a chip for conversion of DC voltages into the AC voltages. Wireless mechanisms also can be used to establish a connection to a power source and to relay signals from the MC electrode. For example, radio signals can be used.

Alternatively, or additionally, external amplifiers can be connected to at least each recording channel set of the MC electrode via the interfacing connector, and more preferably, to each channel of each recording channel set. External multichannel amplifier systems are known in the art and can be connected to the wires of the interfacing connector (which in turn are connected to central terminals) via commercially available connector cables or by DIP sockets to which the interfacing connector is adapted. See, e.g., Bionic Technologies (Salt Lake City, Utah) at www.bionictech.com, and Neuralynx (Tuscon, Ariz.) at www.neuralynx.com. The type of connection will depend on the use of the MC electrode (e.g., whether for an acute or chronic treatment regimen). Preferably, resistors protect the amplifier from damage by static discharge and lowers output noise. Still more preferably, amplifier systems comprise cutoff filters to remove noise from AC signals obtained from the MC electrode which are then converted to DC signals which can be analyzed by a processor.

In one aspect, both internal amplifiers (i.e., within the interfacing connector housing) and external amplifiers are provided. Preferably, an external amplifier is used to amplify a signal already amplified by the internal amplifier or "preamplifier". In one aspect, the preamplifier amplifies a signal 10-50 times (preferably 25 times-50), while the external amplifier amplifies the amplified signal another 50-100,000 times, preferably, at least 1,000 times.

Typically, recorded neural signals include action potentials or "spikes" (brief, voltage transients) which signal the discharge of small groups of cells located near the MC electrode recording channel sets. Because these cells are of different sizes and distances from the channels, their action potentials will vary in shape and amplitude, and may be separated electronically or with computer software (e.g., part of the data acquisition system described further below) on the basis of these differences. Processed signal can be displayed on the display of a computer workstation in communication with the interfacing connection.

Implantable Stimulator/Recording Device

In one aspect, the MC electrode is used in a chronic treatment regimen and is in communication with an implantable, electrically operated source device or stimulator/recording device. Implantable, electrically operated neural stimulator/recording systems are known in the art, and have been used for the control of neural responses to treat intractable pain, epileptic seizures and tremors (e.g., as a result of Parkinson disease). Signals may be transmitted to the implantable devices from external sources such as RF transmitters. RF-coupled neuromodulation systems are easily configured to multiple channels where each channel must be programmed to a different amplitude and which require electrical isolation between the different channels. Further, independent frequency and pulse width can be achieved easily using an RF-coupled stimulator by simply alternatively modulating a carrier wave at two (or more) different frequencies, each frequency value designating a pulse width and rate for a particular channel.

In a preferred aspect, the stimulator/recording device comprises a self-contained power source. For example, one or more batteries can be used. A rechargeable power source with a charging circuit used to convert RF power received by an inductor into a DC voltage or a pure RF powered system can be used (such as the MNT/MNR-916CC system manufactured by Advanced Neuromodulation Systems, Inc. of Allen, Tex.). Where a battery is used, preferably, the stimulator recording device also comprises a micro-controller which monitors battery voltage.

However, more preferably, the system comprises a master controller module having a one or more of: a microcontroller, a telemetry circuit, a power module, a memory (preferably, a remotely programmable memory), a real-time clock, a bus (preferably a bi-directional bus), a plurality of signal modules which are connected to the bus, and circuitry for connecting to the individual channels of MC electrode (e.g., via the interfacing connector).

The signal modules are for inputting signal to the bus and receiving signal from the bus, and can in turn selectively deliver signal to a plurality of leads which are connected to each channel of MC electrode and selectively receive signal from each channel. The signal modules are controlled by instructions from the microcontroller (received via the bus) which in turn can respond to information from the telemetry circuit and the memory. The real-time clock can be used to control at what point signals are delivered from the signal modules to the lead while the telemetry circuit can respond to outside signals from an instrument and/or user monitoring the patient into whom the device is implanted.

In one aspect, signal modules are used to deliver stimuli simultaneously or sequentially (e.g., according to instructions from the processor) to one or more stimulating/lesioning channel sets or STQs of the MC electrode. Different stimulus channel sets can be programmed to deliver electrical pulses having different amplitudes, pulse widths and rates or the same amplitude, pulse widths, and rates as desired by the user.

In one aspect, signals obtained by one or more signal modules (e.g., from recording channel sets or RTQs) are stored in a memory contained within the device (e.g., a non-volatile memory such as a low voltage, serial EEPROM, which is connected to the micro-controller via the bus) and can, in response to comparison of signals to pre-recorded signals, determine whether to start and/or continue and/or to stop delivering stimuli to the one or more stimulating/lesioning channel sets. In one aspect, a user can write into the non-volatile memory when adjustments are made to the stimulation parameters. In a preferred aspect, the impedance of a target site (e.g., neural tissue) is monitored over a period of chronic stimulation (see, e.g., as described in U.S. Pat. No. 5,941,906) to adjust for changes in impedance which occur as a result of chronic stimulation.

The MC electrode and implantable stimulator/recording device also can be used in conjunction to determine and control the appropriate amount of a drug or agent to be delivered to a target site. In one aspect, the MC electrode is used to monitor the electrophysiological responses of one or more cells to a drug delivered at a target site and in conjunction with the master controller, drug/agent delivery is stopped or adjusted in response to this monitoring. For example, when an action potential falls below a predetermined value (indicating decreased cellular activity or death), the telemetry circuit can be used to transmit a command to an implantable fluid delivery pump (described further below) connected to the MC electrode to deliver a volume of drug to the patient as appropriate or to stop or decrease an amount of drug/agent delivery if the drug/agent itself is causing deleterious effects. Similarly, when a cell is hyperactivated (e.g., as a result of seizure activity, for example), the telemetry circuit can be used to transmit a command to the pump to adjust the amount of drug delivered from the MC electrode as appropriate. In one aspect, drug/agent delivery is complemented by electrical stimulation by stimulating channel sets in proximity to the one or more cells. Predetermined values of neural activity can be determined from monitoring the patient during a period when cells have normal activity or can be determined from the activity of cells in a population of normal patients.

Other sensors can be placed in proximity to the MC electrode to enable the MC electrode to monitor physiological activities that do not necessarily relate to the electrical activity of cells at a target site. For example, in one aspect, a glucose sensor is provided in proximity to the MC electrode (e.g., within the lumen of the electrode where the backbone is hollow or on a probe housing placed over the electrode). Preferably, the output signal of the sensor which corresponds to the glucose level is measured by an AC/DC converter (e.g., in communication with the interfacing connector or part of the stimulating system. When the measured glucose level falls below a predetermined value, the master controller telemeters transmit a command to an implantable infusion pump connected to the MC electrode to deliver a volume of insulin to the patient based on the measured level of glucose.

Figure 12:
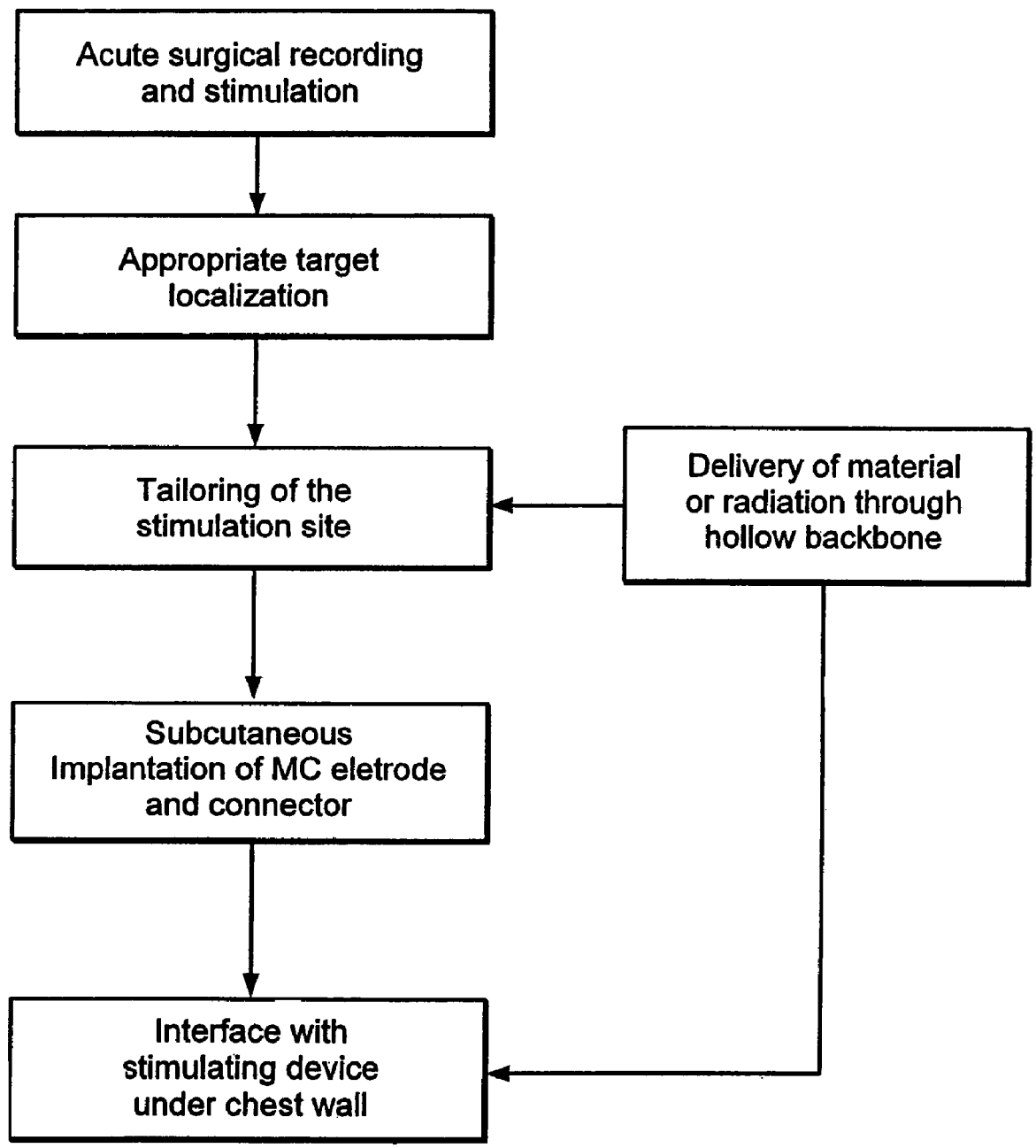
FIG. 12 is a flow chart showing the steps of a method of using an MC electrode in a chronic treatment regimen according to one aspect of the invention.

The flow chart shown in FIG. 12 shows a method by which an MC electrode is implanted at a target site for chronic stimulation of one or more target cells. As shown in the Figure, a reading is obtained initially to appropriately localize a target. The electrode is optimally positioned (e.g., by using the drive system described above). The MC electrode and preferably, the interfacing connector as well, are implanted subcutaneously at the target site and interfaced with the stimulator described above. Drugs can be delivered to the target site via the hollow portion of the MC electrode.

Although the stimulator device has been described as implantable, external devices are known in the art and can be used. For example, in one aspect, the stimulator device is a device which can be carried in a belt as described in U.S. Pat. No. 6,205,359.

Fluid Delivery Pump

As discussed above, a fluid delivery pump can be coupled to an MC electrode which comprises a hollow backbone defining a lumen. In one aspect, the pump is coupled to central opening of the interfacing connector which receives the MC electrode. Preferably, the pump is part of a pump device which comprises one or more controllers and a memory (e.g., such as an EEPROM memory), a container for containing a fluid, and a drive mechanism for forcing fluid from the container into the lumen of the MC electrode. Preferably, the memory is remotely programmable.

In a preferred aspect, the pump is used to deliver an agent such as a drug, and programmed into the memory provided as part of the pump device are delivery parameters related to agent concentration, delivery rate, dose, and bolus size, if appropriate. In one aspect, the container has a label and the device also comprises a label reader for identifying an agent in the fluid which is being delivered and for triggering the controller to run the drive mechanism according to parameters specific for the delivery of that agent.

Fluid delivery pumps, such as used for drug delivery, and their associated control elements, are known in the art, and are described in WO 88/10383; U.S. Pat. Nos. 4,741,732; 6,269,340; and 6,139,539, for example.

Light Sources and Detector Systems

In a particularly preferred aspect, the backbone of the MC electrode provides a light path through which light can be transmitted to a target site and received from a target site to image one or more cells at the target site. In one aspect, the light path can be provided in the form of a light guide or optical fiber. In another aspect, a plurality of optical fibers can be provided (e.g., as bundle within the lumen of a hollow backbone which forms the MC electrode). Bundles of fibers may be used when it is desirable to keep the light transmitting path separate from the light receiving path.

Preferably, the light path is coupled to a light source (e.g., an electromagnetic radiation source (emr), such as a tungsten-halogen lamp, laser, light-emitting diode, and the like). Optical information obtained from the target site can be used to more accurately localize cells in need of stimulation and/or lesioning. In one aspect, the light path is operably connected to a detector, (e.g., such as a photodiode) which detects one or more optical properties of the illuminated target (e.g., neural tissue). Optical properties detectable in the useful range of emr (450-2500 nm), include, but are not limited to, scattering (Rayleigh scattering, reflection/refraction, diffraction, absorption and extinction), birefringence, refractive index, Kerr effect and the like.

Optical properties can be analyzed by the processor which is in communication with the interfacing connector and the MC electrode and other external devices in the system and which is described further below.

Various types of optical detectors may be used, depending on the optical property being detected, the format of data being collected, properties of the area of interest, and the type of application, e.g., surgery, diagnosis, monitoring, and the like. Preferably, the optical detector includes photon sensitive elements and optical elements that enhance or process detected optical signals. Suitable optical detectors include any type of photon detector, such as photodiodes, photomultiplier tubes, cameras, video cameras, charge coupled devices (CCD), and the like. One preferred optical detector for acquiring data in the format of an analog video signal is a CCD video camera which produces an output video signal at 30 Hz having, for example, 512 horizontal lines per frame, e.g., such as a CCD-72 Solid State Camera (Dage-MTI Inc., Michigan City, Ind.) or a COHU 6510 CCD Monochrome Camera with a COHU 6500 electronic control box (COHU Electronics, San Diego, Calif.). The CCD may be cooled, if necessary, to reduce thermal noise.

During optical imaging, a light gathering optical element, such as a camera lens, optical fiber(s), light guide, and the like, can be placed to receive light from a target area and to transmit the light to a suitable detector as described above. Cutoff filters to selectively pass all wavelengths above or below a selected wavelength can be employed. The emr source can be directed to a target site by the light path using a beam splitter controlled by a D.C. regulated power supply (e.g., such as is available from Lambda, Inc.).

Light may be transmitted continuously to a target site or in pulses. For example, non-continuous illumination, such as short pulse (time domain), pulsed time, and amplitude modulated (frequency domain) can be used. Frequency domain illumination sources typically comprise an array of light source elements, such as laser diodes, with each element modulated at 180° out of phase with respect to adjacent elements (see, Chance et al., 1993, *Proc. Natl. Acad. Sci. USA*, 90: 3423-3427). Two-dimensional arrays of light sources comprising four or more elements in two orthogonal planes can be employed to obtain two-dimensional localization information (see, e.g., as described in U.S. Pat. Nos. 4,972,331 and 5,187,672). A scanning laser beam also may be used in conjunction with a suitable detector, such as a photomultiplier tube, to obtain high-resolution images of a target site.

Signals representative of optical properties are produced by the detector upon receiving light from the light path. These are processed by a processor in communication with the detector and preferably, also in communication with the MC electrode and the other external devices of the system. Communication with the processor can be centralized through the interfacing connector described above. Data representing optical properties are displayed on the display of the user device in communication with the processor. In a preferred aspect, signals from the detector are digitized at video speed (30 Hz) and the target is viewed as a digitized image. Analog video signals can be continuously processed using an image analyzer (e.g., such as a Series 151 Image Processor, available from Imaging Technologies, Inc., Woburn, Mass.).

Preferably, consecutive images of target are aligned so that data corresponding to the same spatial location is compared. Small tissue movements can be compensated for by either mechanical and/or computational means as is known in the art. Larger movements can be compensated for by rigidly securing the detector to a stereotactic frame where such a device is used. The detector and light source are preferably provided as an integral unit to reduce their motion relative to each other. Programs implemented by the processor also can be used to align corresponding data. Such programs are known in the art and are described in Goshtasby, 1986, In *Pattern Recognition* 19: 459-66; Wolberg, 1990, "Digital Image Warping" *IEEE Computer Society Press*, Los Alimitos, Calif., for example.

The optical detector preferably provides images having a high degree of spatial resolution at a magnification sufficient to detect single neuronal cells or nerve fiber bundles. Several images can be acquired over a predetermined time period and combined, such as by averaging, to provide images which can be displayed on the display of a user device (e.g., a computer workstation) in communication with the processor. In a preferred embodiment, this image is displayed along side, or superimposed over, a representation of data obtained by recording the electrical activity of one or more cells at the target site.

In addition to obtaining optical information to obtain an image of a target site, optical information can be used to obtain information about the activity of one or more cells at the target site. For example, normally, areas of increased neuronal activity exhibit an increase of the emr absorption capacity of neuronal tissue (i.e., the tissue gets darker if visible light is used for emr illumination, or an intrinsic signal increases in a positive direction). Similarly, a decrease in neuronal activity is indicated by a decrease of emr absorption capacity of the tissue (i.e., the tissue appears brighter, or intrinsic signals become negative). Both negative and positive intrinsic signals from a target site which comprises neural tissue can be monitored using the detector system described above to obtain information relating to neuronal activity. In one aspect, optical information is used to monitor seizure activity at a target site. See, e.g., as described in U.S. Pat. No. 6,233,480.

In a further embodiment, optical imaging is used in conjunction with "electrical imaging" to guide a treatment procedure such as radiation treatment. For example, in order for radiation treatment to succeed in destroying abnormally proliferating cells such as tumors without significant harm to a patient, the location of the target of the treatment must be known precisely, and the radiation source must be aimed precisely at the target. However, it is equally important to know the location and function of non-target cells in the vicinity so as to avoid damage to these. Therefore, in one aspect, the one or more recording channel sets of the MC electrode are used to identify speech, auditory, or visual centers of the brain, to identify cells which generally should not be targeted for treatment. Additionally, or alternatively, the optical imaging system can be used to identify a region of abnormally proliferating cells which should be targeted for treatment. For example, tumor cells often produce unique spectral signals (see, e.g., as described in U.S. Pat. No. 6,104, 945) which can be detected using the optical system.

Processors and Data Acquisition Systems For Signal Analysis

In one aspect, the invention provides a multi-channel data acquisition system and method for the real-time spatial, temporal monitoring and classification of high frequency bandwidth neuronal activity. Surgical targets for the treatment of neurological disorders such as Parkinson's, for example, contain many neurons that have specific neurophysiological electrical properties. Accurate surgical target localization therefore requires the recording of the electrical "signatures" of as many of these neurons as is possible and correlating the electrical signatures with a patient's symptoms and signs before a lesion is made. The use of multi-channel recording electrodes has been shown to increase dramatically the yield of recordable neurons in animals. The task of accurately recording the electrical signatures of the neurons that are picked up by the recording electrodes however, requires a sophisticated, high bandwidth data acquisition system in order to capture the complete waveform of the firing neurons. Although data acquisition systems exist, prior art data acquisition systems have proven to be unsuitable in this environment for large-scale electrophysiological data acquisition.

The present invention provides advantages in that neuronal activity and behavioral events such as associated motor activity of a subject can be recorded. The sorted and classified neuronal and motor activity data can be directly inputted to analysis software that performs on-line power spectral analysis, statistical quantification, and spatial mapping in four-dimensional space (e.g., such as a system similar to the Cheetah Software by Neurallynx, at www.neurallynx.com). The spatio-temporal and neurophysiological characteristics of the recorded neurons can then be used to provide anatomical information about the structures from which the neuronal signals originate thereby allowing the surgical target to be determined directly. Further detailed analysis of the acquired data can also be performed off-line. As a result, the data acquisition system enhances the ability of caregivers and researchers to pinpoint the functional relationships of tasks performed by subjects to the respective regions of brain activity.

Figure 13B:
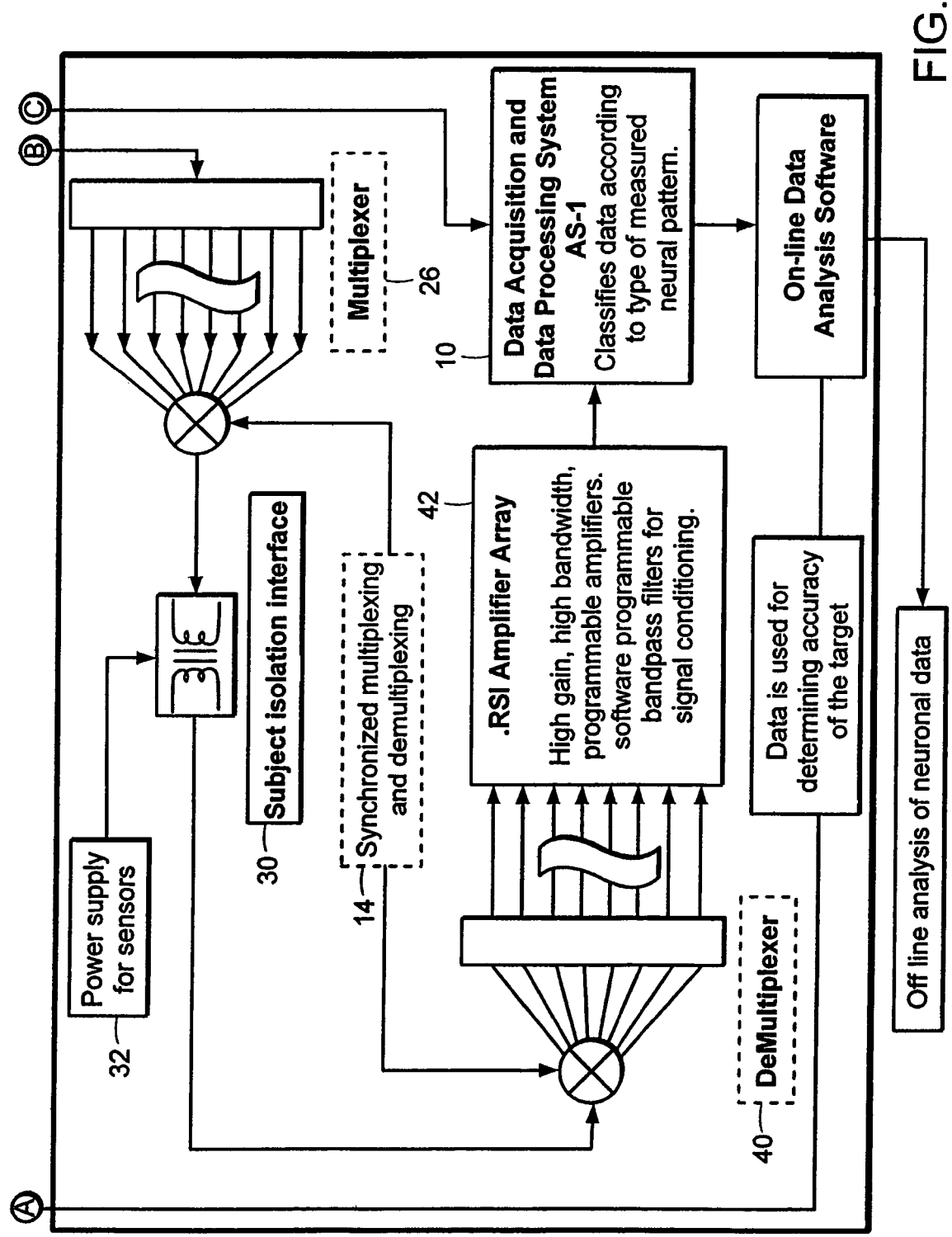
FIG. 13 is a schematic diagram of a data acquisition system according to one aspect of the invention. The inset shows a schematic diagram of an RSI amplifier array forming part of the data acquisition system.

In one aspect, as shown in FIG. 13, a data acquisition and processing system 10 is in communication with an interfacing connector 12, signal processing circuitry 14 coupled to the interfacing connector 12, and a behavioral processor 18 communicating with the data acquisition and processing system 10. Preferably, the interfacing connector 12 is coupled to MC electrode 20 which can be acutely or chronically implanted in a subject's brain to pick up neuronal signals of interest (e.g., such as analog signals). The MC electrode 20 comprises at least one recording channel set which can capture a neuronal electrical event simultaneously on each of the electrode channels provided within the at least one recording channel set. Where four channels are provided, a four dimensional view of a neuronal electrical event may be obtained.

In one aspect, the MC electrode 20 is in communication with an interfacing connector 12 which includes a preamplifier 24 to amplify a neuronal signal output from the MC electrode 20 (i.e., from one or more recording channel sets on the MC electrode). Signal can be further amplified by one or more amplifiers which are external to the interfacing connector and which can be received by signal detectors. Signal detectors can include a Schmitt trigger and flip-flop which can provide a high or low output indicative of whether a signal level has gone over a predetermined threshold during a selected time period (e.g., such as a millisecond interval). Signal detector outputs then can be multiplexed and stored as data in a processor which can convert the signal into a graphic output and perform one or more statistical operations on the signal (e.g., such as histogram analysis). With a compilation of voltage outputs, histograms of electrical activity at many recording sites may be correlated with stimuli. As a result, the response of groups of neurons to stimuli can be studied.

In a preferred aspect, a programmable multiplexer 26 is provided to multiplex amplified multichannel neuronal signal output of the MC electrode 20 onto a twisted shielded cable (not shown) to inhibit noise contamination. Preferably, an isolation element 30 also is provided which acts between a power supply 32 and recording channel set(s) of the MC electrode 20 and includes unidirectional buffer circuits that inhibit backward current leakage from downstream hardware into a subject. This device 30 can be part of the interfacing connector 12. Thus, the isolation element inhibits ohmic contact between the MC electrode 20 and a target site (e.g., such as a subject's brain) and electrically separates the STQ and RTQ. Additionally small optical isolators (not shown) can be provided. These can be incorporated into the interfacing connector 12 or can be provided as a unit external to the interfacing connector 12, e.g., where an acute treatment regimen is contemplated. When the system is used in a chronic treatment regimen, it is preferred that the isolators be provided as part of a subcutaneous unit implanted in a patient.

In one aspect, the preamplifier 24, multiplexer 26, and patient isolation interface device 30, are integrated to form a streamlined arrangement that facilitates interfacing with a subject. This permits neuronal activity to be measured in many environments such as the operating room or chronically. This streamlined arrangement also allows for short wire lengths between the preamplifier 24 and the multiplexer 26, thereby reducing signal loss and noise contamination. In this embodiment, multiple "external" devices are made part of a single unit which includes the interfacing connector 12, e.g., the devices are external to the MC electrode, but are internal within the housing which comprises the interfacing connector 12. For example, the interfacing connector 12 can comprise one or more of a preamplifier 24, A-D converter, multiplexer 26, stimulating and recording circuitry, microprocessors, and the like. This type of arrangement is preferred when the MC electrode 20 is used in a chronic treatment regimen as it facilitates the subcutaneous implantation of the interfacing connector and multiple devices external to the MC electrode.

In one aspect, the interfacing connector 12 is reversibly coupled to an interfacing cable as described above which can be used to connect the interfacing connector 12 to devices external to the interfacing connector 12, e.g., external multi-channel amplifiers or stimulator devices as might be used for an acute treatment regimen, or can be buried at least partially subcutaneously as part of an implanted device used for a chronic treatment regimen.

In a further aspect, the signal processing circuitry 14 also includes a demultiplexer 40 that is synchronized with the multiplexer 26. The demultiplexer 40 demultiplexes the neuronal signals carried on the shielded cable and outputs the neuronal signals onto output channels corresponding in number to the input channels of the multiplexer 26. The signal processing circuitry 14 also can include an RSI amplifier array 42 including high-gain, high bandwidth, programmable differential instrumentation amplifiers and software programmable precision bandpass filters. Filter chips are available from Burr Brown, Texas Instruments, and National Instruments, for example, though they can also be custom-made using methods routine in the art. The amplifiers of the RSI amplifier array 42 amplify the neuronal signals to signal level values that are recognizable by the data acquisition and processing device 10. The bandpass filters of the RSI amplifier array 42 filter the neuronal signals to selectively eliminate parts of the neuronal signals in order to highlight measured signal characteristic features. In one aspect, the filter removes artifacts such as motion artifacts, ground noise, 60 HZ signal noise, and the like.

In one aspect, the RSI amplifier array 42 is highly modularized and includes multiple amplification cards placed on a common back plane. A built-in regulated power supply (not shown) can be used to provide necessary power to the amplification cards. In one aspect, the back plane can hold up to 12 amplification cards. Preferably, each amplification card has the capacity to amplify the neuronal signals from one recording channel set (e.g., such as an RTQ). By adding amplification cards to the back plane, the channel capability of the RSI amplifier array 42 can be increased, making the RSI amplifier array scalable.

In another aspect, each amplification card includes two cascaded amplifying stages per channel to preserve the high bandwidth of the neuronal signals. The gain of each amplifying stage can be programmed through the data acquisition and processing system 16 and can be set to a gain equal to 1, 10, 100, 1,000 or more. Since each amplification card provides two amplifying stages per channel, the amplification factor of each amplification card can be set to a gain equal to 1,100, 10,000 or 1,000,000, or more. Although currently amplification cards have the capability of amplifying a signal up to 1,000,000 times, in one aspect, this final amplification value is deliberately inhibited by the data acquisition and processing device 10, for example, so as not to saturate the system buffers.

The data acquisition system 10 can be coupled to an IBM compatible personal computer running Windows NT. In one aspect, two high-end data acquisition cards, such as those manufactured by Innovative Integration under number ADC64, are installed in the personal computer. The data acquisition cards have high-end digital signal processors (DSPs, not shown) as well as eight 16-bit analog to digital converters (ADCs) that convert signals from the analog domain to the digital domain.

In one aspect, the personal computer executes data acquisition software. In one aspect, the code of the data acquisition software is split into at least two components, namely host code and target code. The host code deals with personal computer functionality while the target code deals with data acquisition card functionality. The host code runs on the personal computer under NT and provides the "front end" or user interface. The target code runs on the data acquisition cards and performs "back end" tasks.

In one aspect, the target code is written in TI C32 DSP Assembly and C. The portion of the target code written in C handles low speed system setting issues and initialization. The portion of the target code written in Assembly runs in a tight loop and forms the basis for a data acquisition algorithm. The data acquisition algorithm is responsible for the task of sampling and multiplexing neuronal signals output by the RSI amplifier array 42 into the ADCs. The Assembly target code also performs "thresholding". Thresholding ensures that the data acquisition cards grab data from the ADCs only if the amplitudes of the neuronal signals received from the RSI amplifier array 42 swing above or below a user-defined threshold. User-defined thresholds will depend on the tissue being recorded from, e.g., the type of neuron being evaluated, its firing properties, etc., as well as on whether the tissue is physiologically normal or involved in a disease process.

In addition, the target code accesses pre-established neuronal signal patterns stored in memory. The target code can be conditioned to compare sampled neuronal signals with the pre-established neuronal signal patterns and generate scores reflecting the degree of similarity between sampled neuronal signals and the pre-established neuronal signal patterns.

In one aspect, the host code is written in Visual C++ and provides a user with control options via a graphical user interface. The host code can grab data sent to it by the target code, analyze and plot the data and save the data to hard disk on cue from a user command. The plots generated by the host code show neuronal signal waveforms and the power spectrum of the neuronal signal waveforms. Additionally, the host code allows the user to set the gains on the data acquisition cards, the gains for the amplifiers of the RSI amplifier array 42, the bandpass filter cut-off frequencies for the RSI amplifier array 42 and the active input channels of the multiplexer 26. In this embodiment, the upper and lower cut-off frequencies of the bandpass filters can be programmed in the range from about 9 kHz to 100 Hz. The host code also allows the user to set the target code threshold.

In one aspect, a behavioral processor 18 is provided which communicates with a plurality of sensors 66 which monitor a subject under observation as the subject performs physical tasks, and records one more physical conditions of the subject during task performance. In this particular embodiment, the sensors 66 include a video recorder, an audio recorder and accelerometers to measure limb movement. Those of skill in the art will, however, appreciate that other types of sensors can be used to monitor the subject. The behavioral processor 18 triggers the data acquisition and processing device 10 so that neuronal activity data acquisition is synchronized with the behavioral events of the subject that are recorded by the behavioral processor 18.

During initialization, the host code of the data acquisition system 10 checks for the presence of the data acquisition cards in the personal computer. When the data acquisition cards are present, the host code downloads the target code onto the data acquisition cards and sets up a "handshaking" mechanism between the host code and the target code to enable data and command transfer between the host code and the data acquisition cards.

During operation, an MC electrode 20 is implanted at a target site, such as in the subject's brain. In a preferred aspect, the MC electrode comprises at least one recording channel set comprising four electrodes or an RTQ which can acquire neuronal activity at target site in four dimensions. Sensors 66 are also initialized to monitor behavioral events of the subject under observation. The subject is then requested to perform tasks. During task performance, the behavioral processor 18 records the output of the sensors 66. The behavioral processor 18 also sends "acquire" and "stop-acquire signals to the data acquisition device and processing device 10 at selected times during task performance so that neuronal activity, corresponding to selected instances of subject motor activity, is acquired over the desired durations. These durations may be from several seconds to several minutes in duration.

During task performance, the neuronal signal output of the MC electrode 20 is conveyed to the preamplifier 24. The preamplifier 24 in turn amplifies the neuronal signals to signal levels in the range of from about 0 to ±10 V to reduce signal loss either by decreasing the output impedance to increase current or by providing gain to increase voltage and current. The amplified neuronal signals output by the preamplifier 24 are applied to the input channels of the multiplexer 26. The neuronal signals received on the active input channels of the multiplexer 26 are multiplexed onto the shielded twisted cable before being conveyed to the patient isolation interface device 30. As mentioned previously, the patient isolation interface device 30 inhibits ohmic contact between the MC electrode 20 and the subject's brain.

The neurons signal output of the patent isolation interface device 30 is conveyed to the demultiplexer 40 via the cable and demultiplexed onto its output channels. The RSI amplifier array 42 in turn boosts the signals appearing on the output channels of the demultiplexer 40 by providing EMI and RF noise regeneration in the neuronal signals in accordance with the values assigned to the programmable gains of the amplifiers by the data acquisition and processing device 10. The RSI amplifier array 42 also removes selected pans of the neuronal signals via the bandpass filters as programmed by the data acquisition and processing device 10. The amplified and filtered neuronal signals output by the RSI amplifier array 42 are then conveyed to the data acquisition and processing device 10.

When the data acquisition and processing device 10 are triggered by an acquire signal from the behavioral processor 18, the target code is executed. When the target code is executed, the data acquisition cards step through the data acquisition algorithm. During this algorithm, the neuronal signal output of the RSI amplifier array 42 is sampled at a rate equal to about 30 kHz (resultant) and the neuronal signals are multiplexed into the ADCs. The neuronal signals are in turn digitized by the ADCs. During execution of the target code, thresholding is also performed by comparing the digital values output by the ADCs with the user set threshold.

If the digital values on one or more of the RSI amplifier array output channels swing above or below the threshold signifying potentially relevant neuronal signals, the data acquisition cards capture the digital values for a predetermined period of time, in this example 1-2 msecs. Specifically, the data acquisition cards store the previous eight sampled values in addition to the next twenty-four (24) sampled values. This is achieved by using circular buffers to store the sampled data while it is being acquired. For the acquisition of data to take place at 30 kHz, the Assembly target code performs an acquisition once every 90 KHz. If the target code is conditioned to compare incoming neuronal signals with the pre-established neuronal signal patterns stored in memory, the target code compares the digital values with each of the stored patterns and generates scores. The sampled digital values, the threshold information signifying the transducer that generated the neuronal signal which caused the digital value to be sampled, and the scores, if calculated, form a data packet.

In one aspect, once seven data packets are grabbed by the data acquisition cards, the data packets are transferred in bursts or streams to the host code via a PCI bus within the personal computer and stored in permanent memory. A burst is sent per PCI bus mastering operation for a total data throughput of 20 Mbs, a rate well under the permissible PCI bus transfer limit of 68 Mbs.

The host code in turn processes the data on-line by performing power spectral analysis, statistical quantification and spatial mapping in four dimensions. Thus, real time feedback can be provided to improve surgical targets and to modify the active channels of the multiplexer 26. The data stored in memory can also be downloaded to an off-line neural data analysis system for further processing.

When the duration of the relevant behavioral event has expired, the behavioral processor 18 sends a "stop-acquire" signal to the data acquisition and processing device 10 causing it to stop the data acquisition. At this point the neuronal signals output by the MC electrode 20 is no longer recorded.

The above-described form of data gathering accomplishes two goals. First, the temporal sequence of neuron firing is clearly established relative to the stages of the behavioral event of interest. Secondly, the spatial location of each of these neurons firing in sequence is clearly established by the bundled electrodes of the recording probes. The collected data is readily available for processing by data analysis techniques to yield insight into the nature of the neural activity in relationship to behavioral patterns. This immediate data analysis can be used to determine the properties of recorded neuronal activity and therefore, increase the accuracy of surgical targets, which aids in patient treatment.

Methods of Using MC Electrodes

The quality of data about neuronal group interactions obtained from multichannel electrodes is directly related to the number of simultaneous recordings made. It is desirable, for example, to sense the electrical activity of neurons at twenty or more sites through the cortex, the outer layer of the brain. The simultaneous response of neighboring neurons to stimuli provides a greater insight into the group interaction of neurons and a more detailed characterization of a target site for stimulation and/or lesioning or drug delivery.

The MC electrode according to the invention is particularly suitable for sensing electrical activity of brain tissue at a plurality of sites because its volume is small enough to minimize damage to the tissue. The increased number of sites which can be tested without trauma to the brain increases the efficiency of neurosurgical procedures since targets can be localized more effectively and safely.

The recording and stimulation function of the MC electrode also facilitates automatic feedback control by a processor in communication with the MC electrode. This technique, which is well known to those specialized in the treatment of epileptic seizures, involves monitoring brain activity signals and accurately identifying aberrant electric activity. After analysis, electrical current is administered back to the brain in opposition to the original aberrant level so that the net resultant voltage, current and/or electrical field in localized areas on the brain is maintained at no level greater than that experienced normally. Because the MC electrode can be implanted (vs. used at the surface of the brain), electrical signals from target cell(s) can be recorded by the recording channel set(s) of the electrode without any deterioration of signal (e.g., such as due to the impedance of the fluids, tissue, skull bone and other media between the target site and electrode as would occur when using a surface electrode). Similarly, a control signal for feedback data, if applied externally, would require a larger electrical signal to produce a comparable control.

Typical electrical voltages represented in medical research studies reveal that, when monitored internally, a normal brain pattern signal can reach 10 millivolts while the same signal monitored outside the skull produces a level of approximately 10 microvolts. For example, the aura condition of an epileptic seizure can in fact increase the electrical activity a factor of 10 times to a level 100 millivolts (when monitored internally). Hence, for a corrective signal to be applied in opposition to such an aberrant level, a minus 90 millivolts level would be internally applied whereas approximately minus 90 volts would be externally applied; a quantity which could be dangerous. Therefore, MC electrodes provide optimal voltage control at low levels that are safe.

The type of stimulation delivered by the MC electrode depends on the specific location at which the electrode is surgically implanted and the desired action on cells at that location. Preferably, the MC electrode delivers stimuli having amplitudes of 0.1 to 20 volts, pulse widths varying from 0.02 to 1.5 milliseconds, and repetition rates varying from 2 to 2500 Hz. If the cell is a neuron and activity is to be blocked, preferably, the frequency of the stimulus is in the range 50 to 2500 HZ. If the neuronal activity is to be increased, the frequency is preferably, in the range of 2 to 100 Hz. The invention therefore provides a method of monitoring the activity of one or more cells at a target site by recording electrical potentials of the one or more cells and/or modulating the activity of one or more cells. In one aspect, the method comprises bringing an MC electrode, as described above, in electrical proximity to the one or more cells and recording the activity of the one or more cells using at least one recording channel set (e.g., such as an RTQ) of the MC. Preferably, this recorded activity is compared to the activity of a cell with one or more known physiological properties (e.g., a non-diseased neural cell). In one aspect, the recorded activity is used to determine the anatomical location of one or more malfunctioning cells. In a preferred aspect, after determining the anatomical location of the one or more malfunctioning cell, at least one other set of channels (e.g., a stimulating/lesioning channel set, such as an STQ) is activated to deliver an electrical stimulus to the one or more cells. This may require repositioning the MC electrode prior to stimulation and recording at a new position to validate that a target cell(s) is in suitable electrical proximity to a stimulating/lesioning channel set or STQ. In one aspect, the stimulus is used to activate the one or more cells. In another aspect, the stimulus is used to inhibit the one or more cells. In a further aspect, the stimulus is used to disable or lesion the one or more cells.

Preferably, a processor in communication with the MC electrode is used to control the movement and activity of the electrode. In a particularly preferred aspect, the MC electrode is used to image a target site and the processor moves and/or alters the activity of the electrode in response to an image obtained (i.e., automatically and/or or in response to instructions from a user).

For example, in one aspect, the MC electrode is used in an acute treatment by bringing the MC in proximity to one or more cells, localizing target cells in need of such treatment (e.g., using at least one RTQ), bringing the MC in closer proximity to the cells if necessary, activating or inhibiting the activity of the target cells or disabling the target cells (e.g., using at least one STQ) and removing the MC electrode from the proximity of the target cells.

In another aspect, the MC electrode is used in a chronic treatment by bringing the MC in proximity to one or more cells, localizing target cells in need of such treatment (e.g., using at least one RTQ), bringing the MC electrode in closer proximity to the cells if necessary, and activating or inhibiting the activity of the target cells (e.g., using at least one STQ). Preferably, the MC electrode remains in proximity to the target cells to monitor the activity of the target cells and stimulating the cells as necessary to maintain a desired state of the cells.

In a particularly preferred aspect of the invention, the MC electrode is used to treat Parkinson's disease. Parkinson's disease is a neuropathological condition of unknown etiology which afflicts approximately 1 million individuals in the U.S. alone. Symptoms include a decreased spontaneous movement (bradykinesia), rigidity, and tremor, which in many cases can be very disabling.

In one aspect, therefore, the method comprises inserting an introducer tube (e.g., contained within a stereotactic frame) into the brain of a patient having Parkinson's disease such that the distal end of the tube is positioned close to the target tissue (e.g., as determined by CT, MR or a tomographic scanning method). An MC electrode according to the invention is next introduced into the introducer tube and is connected to a drive mechanism as described above via the interfacing connector. The tip of the electrode is advanced and the degree of advancement may be adjusted in based on information about optical properties of the target site obtained from a detector in communication with a light path (e.g., optical fiber) provided either within the MC electrode backbone or as part of the MC electrode backbone. These optical properties are then converted into an image on the display of a user device in communication with a processor which in turn is in communication with the detector, interfacing connector, and drive for controlling the movement of the MC electrode.

Preferably, the MC electrode is driven through a trajectory defined by the processor within the globus pallidus of the brain based on instructions from a user upon viewing the image and displays of electrical signals obtained from RTQ channels of the MC electrode. The MC electrode is used to monitor the physiological activity of at least one neuron within the globus pallidus within the vicinity of the MC electrode using at least one recording channel set (e.g., RTQ). In response to this monitoring, the processor can then inactivate the at least one neuron by applying an appropriate degree of stimulation to the at least one neuron (see, e.g., as described in Lehman et al., 2000, Stereotact. *Funct. Neurosurg.* 75(1): 1-15).

For example, the MC electrode can be used to identify the abnormal cells in the globus pallidus interna and subthalmic nucleus, and/or in the pedunculopontine nucleus in a patent with Parkinson's disease by their high frequency of firing (e.g., 30-120 Hz) and these cells can be inactivated by applying a electrical discharge from one or more stimulating sets of the MC electrode in a frequency range of from 50-200 Hz, with a voltage range of 1-5V, and currents in the 100-500 µAmp range.

In addition to inactivating cells, different levels of stimulation may be used to prevent or reduce excitatory damage caused by high firing rates. Hence, in addition to helping symptoms directly, stimulation may also help slow down the progression of disease. In addition, the ability to micro-stimulate using recording channel set(s) of the MC electrode can help identify areas around the electrode that are vulnerable and should be avoided. Lesioning in several areas that are consistently active also can be performed using the MC electrode. The areas targeted can be single or multiple.

Administration of growth factors through the hollow portion, along with tissue suspensions may also help treat and reverse the difficulties in Parkinson's disease. In this scenario, multiple injections into physiologically defined areas can be made. If the MC electrode is left in situ, the injections can be carried out over a period of time instead of having to re-perform surgery.

In addition to Parkinson's disease, electrode stimulation has been used to treat a number of different diseases including, but not limited to: motor dysfunction (see, e.g., U.S. Pat. No. 6,175,769); spasticity (see, e.g., Lin, 2000, *Neurorehabil. Neural Repair* 14(3): 199-205; Davis, 2000, *Arch. Med. Res.* 31(3): 290-9); tremors (Krauss et al., 2001, *Neurosurgery.* 48(3): 535-41; discussion 541-3); dystonia (see, e.g., Krack 2001, *Eur. J. Neurol.* 8(5): 389-99); mood disorders (see, e.g., U.S. Pat. Nos. 6,263,237; 6,167,311); hypothalmic obesity (see, e.g., U.S. Pat. Nos. 5,540,734; 5,443,710; and U.S. Pat. No. 4,646,744); incontinence (see, e.g., U.S. Pat. No. 5,314,465); stroke (see, e.g., U.S. Pat. No. 6,221,908); epilepsy (see, e.g., U.S. Pat. No. 6,205,359); chronic pain (see, e.g., Van Buyten et al., 2001, *Eur. J. Pain* 5(3): 299-307); spinal cord injuries (Prochazka et al., 2001, *J. Physiol.* 533(Pt 1): 99-109).

The invention contemplates that the MC electrodes according to the invention can be used in methods of treating these disorders by bringing an MC electrode in proximity to a target site (as identified in any of the above references), recording electrical signals of cells at a target site to identify cells with abnormal electrical activity (as described, for example, in any of the above references) and delivering an appropriate amount of electrical stimulation to restore the electrical activity of the target cells to a predetermined normal level (e.g., as described in the references above or as determined by monitoring the activity of cells during a period of normal physiological activity or by monitoring cells which neighbor a target site and which display normal physiological activity).

For example, thalamic stimulation or lesioning by the MC electrode can be used for modulation of tremor. Tremor cells, identified behaviorally in the operating room and chronically as having higher frequency of firing and rhythmically related to the tremor, may be recorded using the MC electrode. Once identified, stimulation or lesioning at multiple sites can be performed to reduce the output of these cells, thereby producing an arrest of tremor.

In another aspect, abnormal firing of cells in the cortex can be determined as a means of identifying seizure activity in patients with epilepsy. Micro-stimulation can be performed in the areas to reproduce symptoms, such as epileptic auras. In addition, the border zones of areas of abnormality can be identified well. This procedure currently requires open craniotomy. In one aspect, multiple small MC electrodes according to the invention can be navigated underneath the skull through a small opening. The visualization capability of the MC electrodes (e.g., the presence of one or more light paths, cameras, and or lens, which are part of, or internal to, the backbone) allows precise placement of the MC electrodes. Central guide wiring can be placed to allow manipulation of the electrodes. The electrode(s) can then be left in place if necessary, once region(s) of interest are identified. This procedure may allow the surgeon to preserve brain tissue instead of having to take the epileptogenic areas out.

Additionally, drugs that reduce epileptic potential can be administered once physiologically active areas are identified. These areas may not simply be in the cortex, but also may be in other structures such as the thalamus, hippocampus, other deep brain structures, vagal nerve, and the like, that provide an origin for the epileptic spikes.

The MC electrode according to the invention also can be used to implement tumor surgery. For example, abnormal tissue can be identified using the optics of the electrode (e.g., surface and deep tumors, ventricular tumors, and the like). Additionally, or alternatively, the tumor cells may demonstrate particular electrical signatures which can be identified using recording channel sets of the electrode and correlated with the presence of abnormal cell proliferation. In one aspect, suction is applied through the hollow central core of the MC electrode and fluid is withdrawn through the core, to provide one or more samples to test for the presence of tumor markers.

Electrically normal cells also can be identified to mark the borders of the tumor through the placement of multiple MC electrodes. This is especially useful to identify areas adjacent to abnormally proliferating cells which may have critical functions, e.g., such as the visual or speech control centers of the brain. Once the tumor is properly identified, lesioning or administration of chemotherapy or radiation therapy is feasible. This is dependent on factors such as the tumor cell type, its location and its chemo and radiosensitivity.

In addition to using the MC electrode in methods of treatment, the MC electrode can be used to detect the presence of, or monitor the progression of, abnormal physiological activity in a cell. In one aspect, the target site is the brain and the MC electrode is used to detect the presence of abnormal activity in target sites such as the Locus Ceruleus; Amygdyla; Nucleus of Thalamus; subthalamus; subthalamic nucleus; pedunculopontine nucleus; Dorsal raphe Nucleus; Septum; Cortex; hippocampus, Anterior Thalamus; Mamillary body, Globus Pallidus, cranial nerve (e.g., the vagus nerve), and the like. In another aspect, the target site is the spinal cord. In a further aspect, the MC electrode is used to monitor the electrical activity of cells at a target site in order to control drug delivery to the target site.

EXAMPLE

The invention will now be further illustrated with reference to the following example. It will be appreciated that what follows is by way of example only and that modifications to detail may be made while still falling within the scope of the invention.

Example 1

Design and Testing of Four Channel Prototype Electrodes

Figure 5:
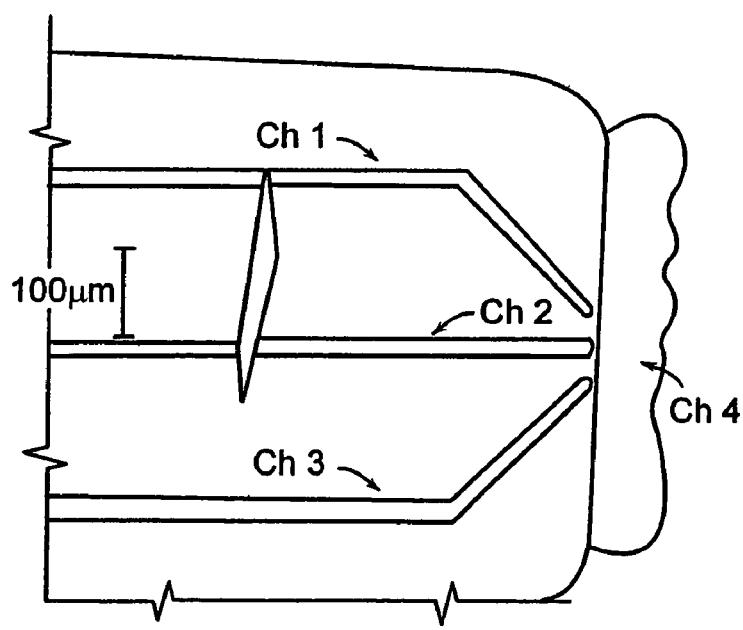
FIG. 5 shows the geometry of the tip of the MC electrode shown in FIG. 4.

A gold plated copper-backed flex circuit board was first glued onto a gold-coated metal rod backbone. Three of the four channels were precisely machined using a depth control machining technique on the circuit board leaving the underneath plastic insulating material intact. The board was then mounted on to a 0.5 mm diameter gold-coated metal rod backbone with a fourth channel machined on it. Electrode connector pads were attached to wires for data measurements (see, FIG. 4). The machined width of the individual channels of the electrode was 15±2 μm. The electrode was then partially covered with an insulating plastic material leaving 4±1 μm of the tip uninsulated. The spacing between the four channels at the tip was 20±5 μm (see, FIG. 5).

Figure 6:
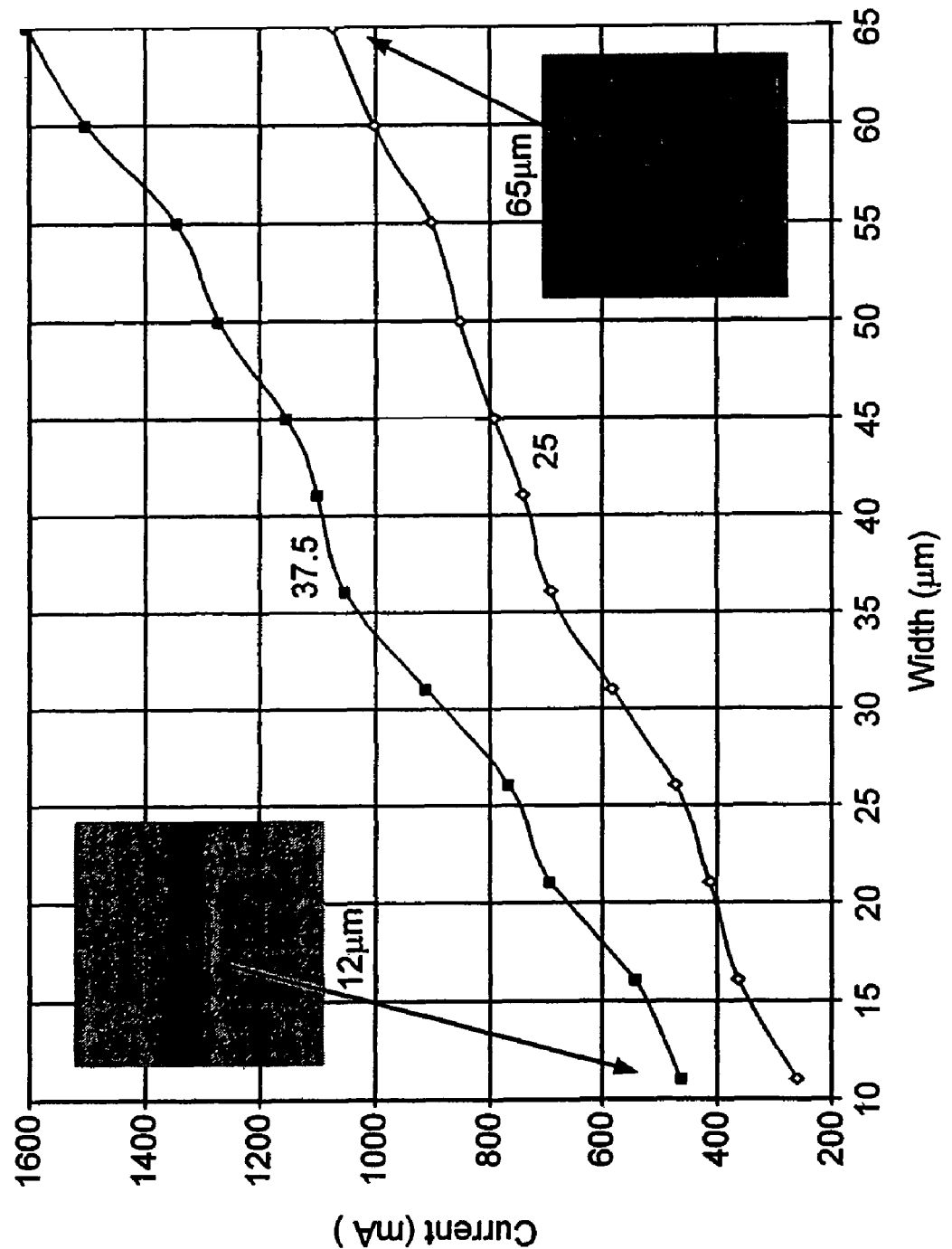
FIG. 6 is a graph showing change in current as a function of channel width.

To determine the amount of current deliverable through fine wire cross-sections of varying diameters measurements were initially performed on 25 μm and 37.5 μm diameter copper-gold flex backbones having channels whose widths ranged from 12 μm to 65 μm (see, FIG. 6). The maximum possible current was passed through each conductor width for each type of backbone. Even with a minimal channel width of 12 μm, a single channel could withstand continuous current levels as high as 250 mA and 460 mA for conducting materials thickness of 25 µm and 37.5 µm, respectively. This current quantity is more than sufficient to stimulate or produce lesions.

Figure 7:
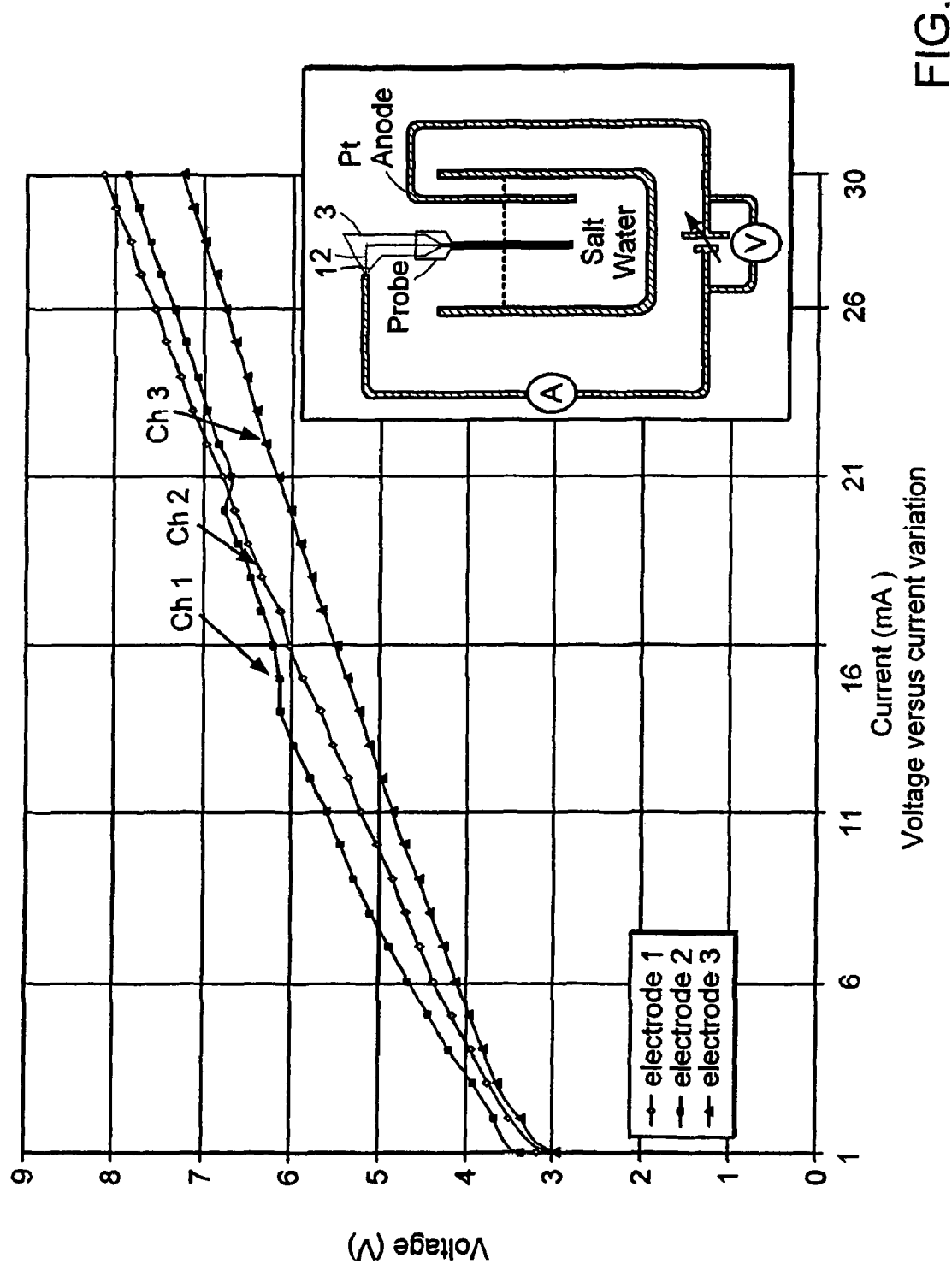
FIG. 7 is a graph showing changes in voltage as a function of current variation through an MC electrode according to one aspect of the invention.

Voltages versus current characteristics were tested for each independent channel (see, FIG. 7) and the measured voltage with respect to input was plotted for each channel. Each individual channel of the electrode was used as a cathode with a copper cylindrical support as the anode. The completed assembly was inserted into salt solution for data measurements (see insert in FIG. 7). As shown in FIG. 7, there is a linear relationship between the voltage and current in the channels of the MC electrode. The measurements also indicate chat it is indeed possible to use current levels beyond 10 mA through each individual channel of the electrode. Additional measurements were carried out using a platinum electrode as anode and the measured data showed a linear increase in the current levels >30 mA (data not shown).

Figure 8:
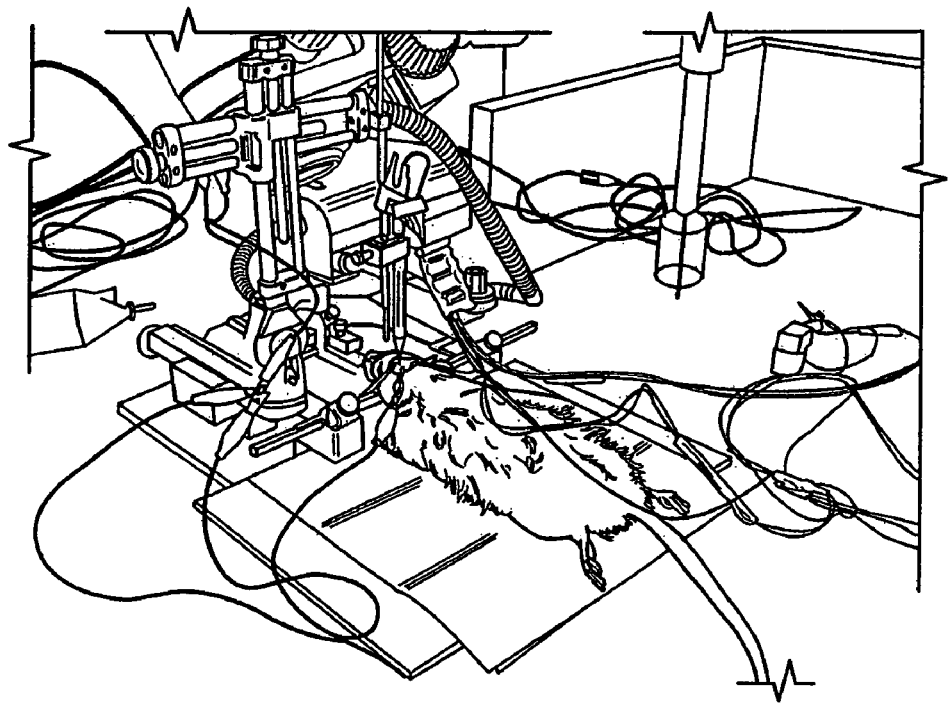
FIG. 8 shows an animal connected to an MC electrode which is in communication with a data acquisition system according to one aspect of the invention.
Figure 9:
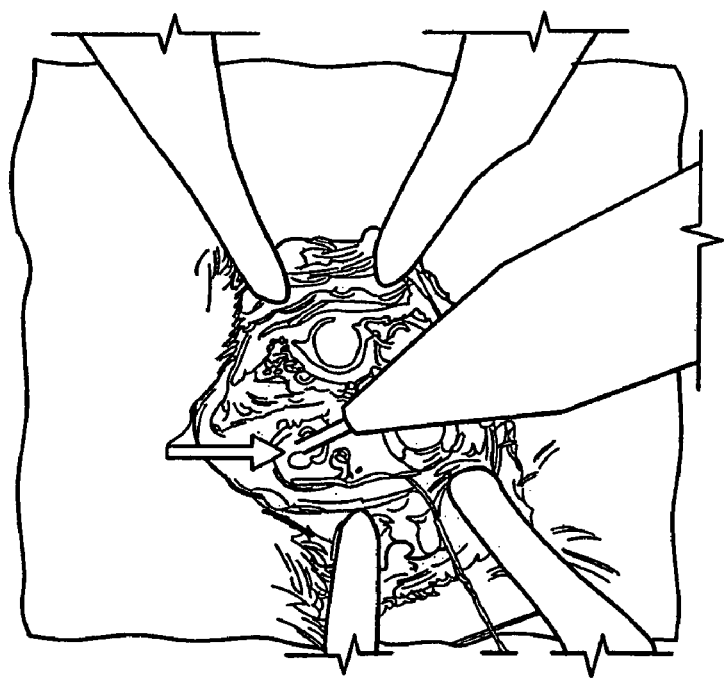
FIG. 9 shows an MC electrode according to one aspect of the invention penetrating the brain of a rodent.

The MC electrode was then tested in a rodent to determine its ability to record in vivo neuronal signals. An anesthetized animal was prepared according to procedures well known in the art (see, FIG. 8) and the electrode was inserted into the brain of the animal (FIG. 9). The outputs of the electrode were connected to the data acquisition system described herein.

Figure 10:
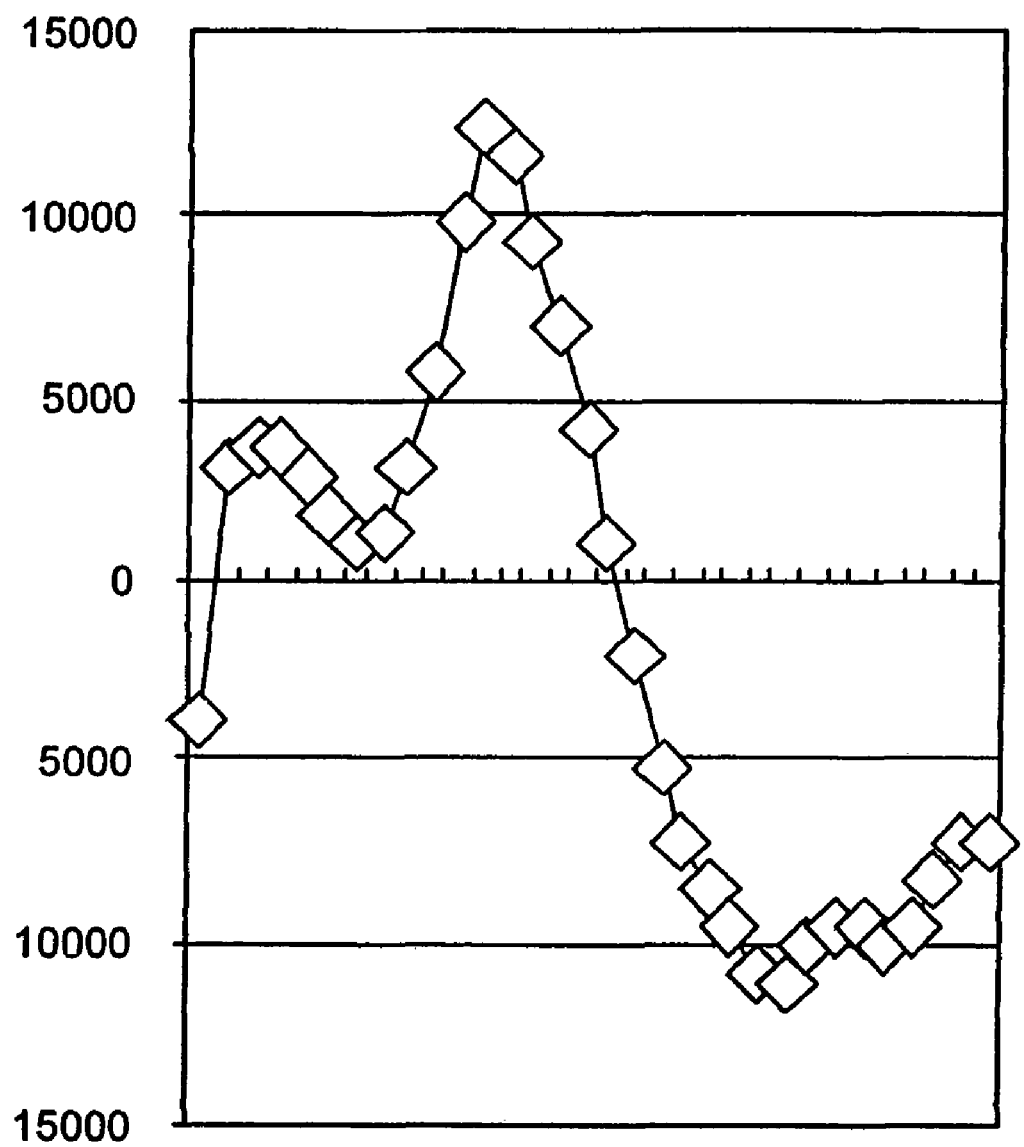
FIG. 10 shows a single neuron spike (time 200 µs/div versus voltage 50 µV/div) recorded using an MC electrode in vivo according to one aspect of the invention.
Figure 11:
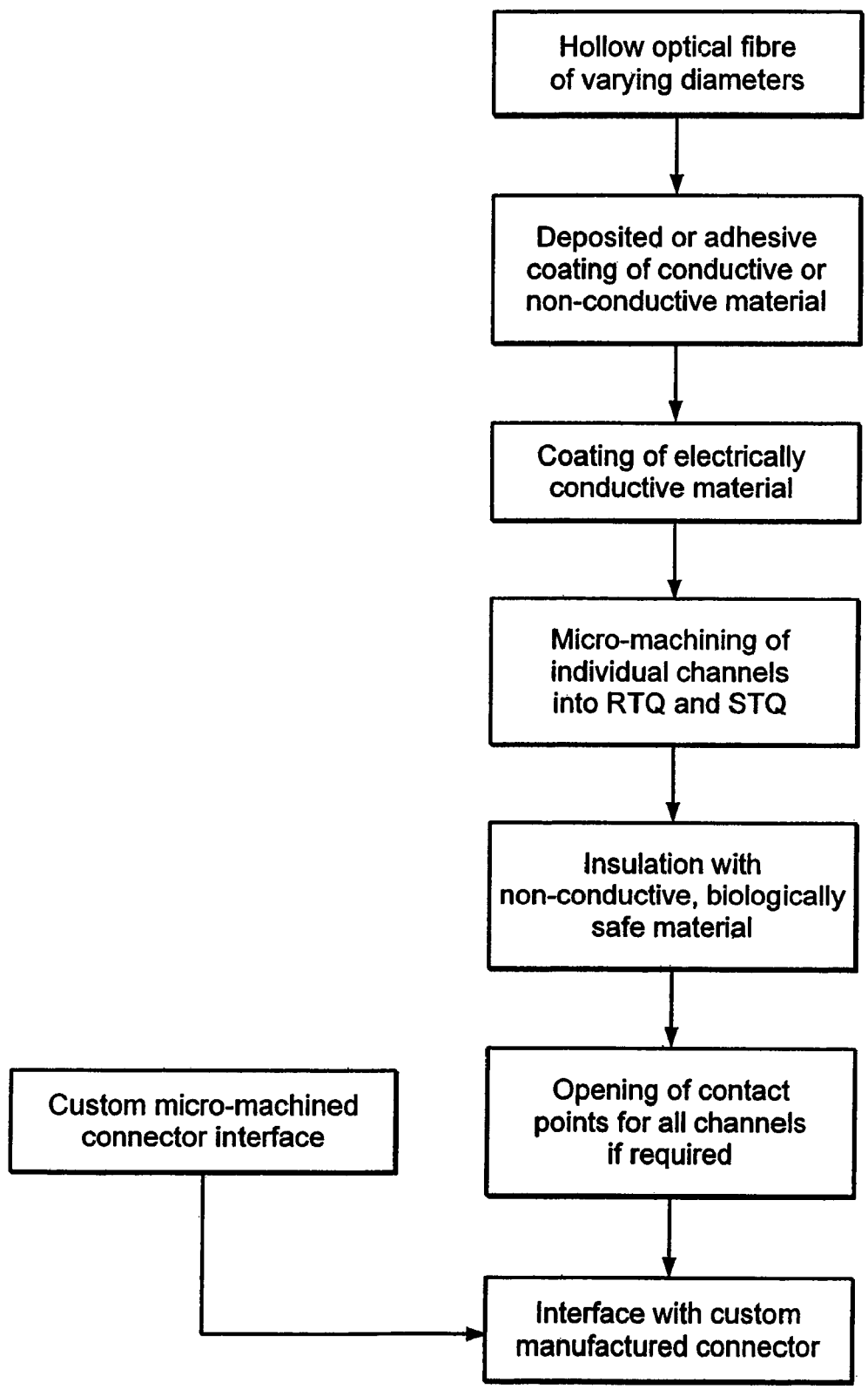
FIG. 11 is a flow chart showing the steps used to fabricate an MC electrode according to one aspect of the invention.

A typical neuronal recording is shown in FIG. 10. The Figure shows that the four-channel MC electrode is capable of passing significant amounts of current into the brain of an animal for recording neural signals and/or for stimulating and/or lesioning neural cells at a target site. Multiple four-channel bundles with individual channels for stimulation and recording can be fabricated on an MC electrode.

Variations, modifications, and other implementations of what is described herein will occur to those of ordinary skill in the art without departing from the spirit and scope of the invention.

All of the references identified herein, are hereby expressly incorporated herein by reference.

What is claimed is:

1. A method of fabricating a multichannel electrode, said method comprising the steps of:
   a) providing a first non-planar backbone comprising a lumen;
   b) coating said non-planar backbone with an electrically conductive material;
   c) laser micro-machining a plurality of channels into said electrically conductive material;
   d) providing a second non-planar backbone within said lumen of said first non-planar backbone, said second non-planar backbone coated with an electrically conductive material and comprising a plurality of electrode channels machined thereon; wherein at least one channel of said multichannel electrode comprises an impedance suitable for recording electrical activity of a cell, and wherein at least one channel comprises an impedance suitable for stimulating the electrical activity of a cell; and
   (e) placing said second backbone within said lumen of said first backbone.

2. A method of fabricating a multichannel electrode, said method comprising the steps of:
   a) providing a first non-planar backbone comprising a lumen;
   b) coating said non-planar backbone with an electrically conductive material;
   c) laser micro-machining a plurality of channels into said electrically conductive material;
   d) providing a second non-planar backbone comprising a lumen within said lumen of said first non-planar backbone, said second non-planar backbone coated with an electrically conductive material and comprising a plurality of electrode channels machined thereon; wherein at least one channel of said multichannel electrode comprises an impedance suitable for recording electrical activity of a cell, and wherein at least one channel comprises an impedance suitable for stimulating the electrical activity of a cell, and/or lesioning a cell; and
   (e) placing said second backbone within said lumen of said first backbone.

3. The method of claim 1 or 2, wherein said impedance suitable for stimulating the electrical activity of a cell is less than or equal to 200 kilo ohms.

4. The method of claim 1 or 2 wherein said impedance suitable for recording electrical activity of a cell is from 200 kilo ohms to one megaohm.

5. The method of claim 1 or 2, wherein said impedance suitable for lesioning that is less than or equal to 200 kilo ohms.

* * * * *